United States Patent
Gardner, II et al.

(10) Patent No.: US 9,408,922 B2
(45) Date of Patent: Aug. 9, 2016

(54) ANTI-TOFACITINIB ANTIBODIES AND USES THEREOF FOR DRUG MONITORING

(71) Applicant: Pfizer Inc., New York, NY (US)

(72) Inventors: Joseph Paul Gardner, II, Colchester, CT (US); Victoria Yatsum Wong, East Lyme, CT (US)

(73) Assignee: Pfizer Inc., New York, NY (US)

( * ) Notice: Subject to any disclaimer, the term of this patent is extended or adjusted under 35 U.S.C. 154(b) by 32 days.

(21) Appl. No.: 14/411,356

(22) PCT Filed: Jun. 18, 2013

(86) PCT No.: PCT/IB2013/055008
§ 371 (c)(1),
(2) Date: Dec. 24, 2014

(87) PCT Pub. No.: WO2014/001967
PCT Pub. Date: Jan. 3, 2014

(65) Prior Publication Data
US 2015/0337054 A1      Nov. 26, 2015

Related U.S. Application Data

(60) Provisional application No. 61/665,361, filed on Jun. 28, 2012.

(51) Int. Cl.
*C07K 16/44*     (2006.01)
*A61K 47/48*     (2006.01)
*G01N 33/94*     (2006.01)

(52) U.S. Cl.
CPC ....... *A61K 47/48284* (2013.01); *A61K 47/4833* (2013.01); *C07K 16/44* (2013.01); *G01N 33/9493* (2013.01); *C07K 2317/10* (2013.01); *C07K 2317/30* (2013.01); *C07K 2317/33* (2013.01); *C07K 2317/56* (2013.01); *C07K 2317/565* (2013.01); *C07K 2317/92* (2013.01)

(58) Field of Classification Search
CPC ................ A61K 47/48284; A61K 47/4833; G01N 33/9493
See application file for complete search history.

(56) References Cited

PUBLICATIONS

Paniagua et al., "Quantitative analysis of the immunosuppressant CP-690,550 in whole blood by column-switching high-performance liquid chromatography and mass spectrometry detection." Therapeutic Drug Monitoring, vol. 27, No. 5, p. 608-616 , 205.
Tamura et al., A Highly sensitive method to assay FK-506 levels in plasma., Transplantation Proceedings, vol. 19, No. 5, p. 23-29, 1987.
Matsumoto et al. "Preparation of antibodies against a novel immunosuppressant, FTY720, and development of an enzyme immunoassay for FTY720." Bioorganic & medicinal Chemistry, vol. 14, No. 12, p. 4182-4192, 2006.
Clementi et al., "Antibodies Against Small Molecules", Annali Dellistituto Superiore Di Sanita, Rome, vol. 27, No. 1,p. 139-144, 1991.
Flanagan et al., "Discovery of CP-690,550: A Potent and Selective Janus Kinase (JAK) Inhibitor for the Treatment of Autoimmune Diseases and Organ Transplant Rejection." J. of Medicinal Chemistry, American Chemical Society, vol. 53, No. 24., p. 8468-8487, 2010.
Lefranc, et al., "IMGT, the international ImMunoGeneTics database." Nucleic Acids Res., vol. 27, No. 1 p. 209-212, 1999.
MacCallum et al., Antibody-antigen Interactions: Contact Analysis and Binding Site Topography. J. Molecular Biol., vol. 262, p. 732-745, 1996.
Makabe et al., "Thermodynamic Consequences of Mutations in Vernier Zone Residues of a Humanized Anti-human Epidermal Growth Factor Receptor Murine Antibody, 528." J. Biological Chemistry, vol. 283, No. 2, p. 1156-1166, 2008.

*Primary Examiner* — Shafiqul Haq
(74) *Attorney, Agent, or Firm* — Pfizer Patent Department; Raquel M. Alvarez

(57) ABSTRACT

The invention provides selective tofacitinib antibodies, immunogenic tofacitinib conjugates that are useful as immunogenic molecules for the generation of antibodies specific for tofacitinib, along with methods for measuring the concentration of tofacitinib in a sample, processes for making the antibodies, and assays and kits for using the antibodies.

23 Claims, 5 Drawing Sheets

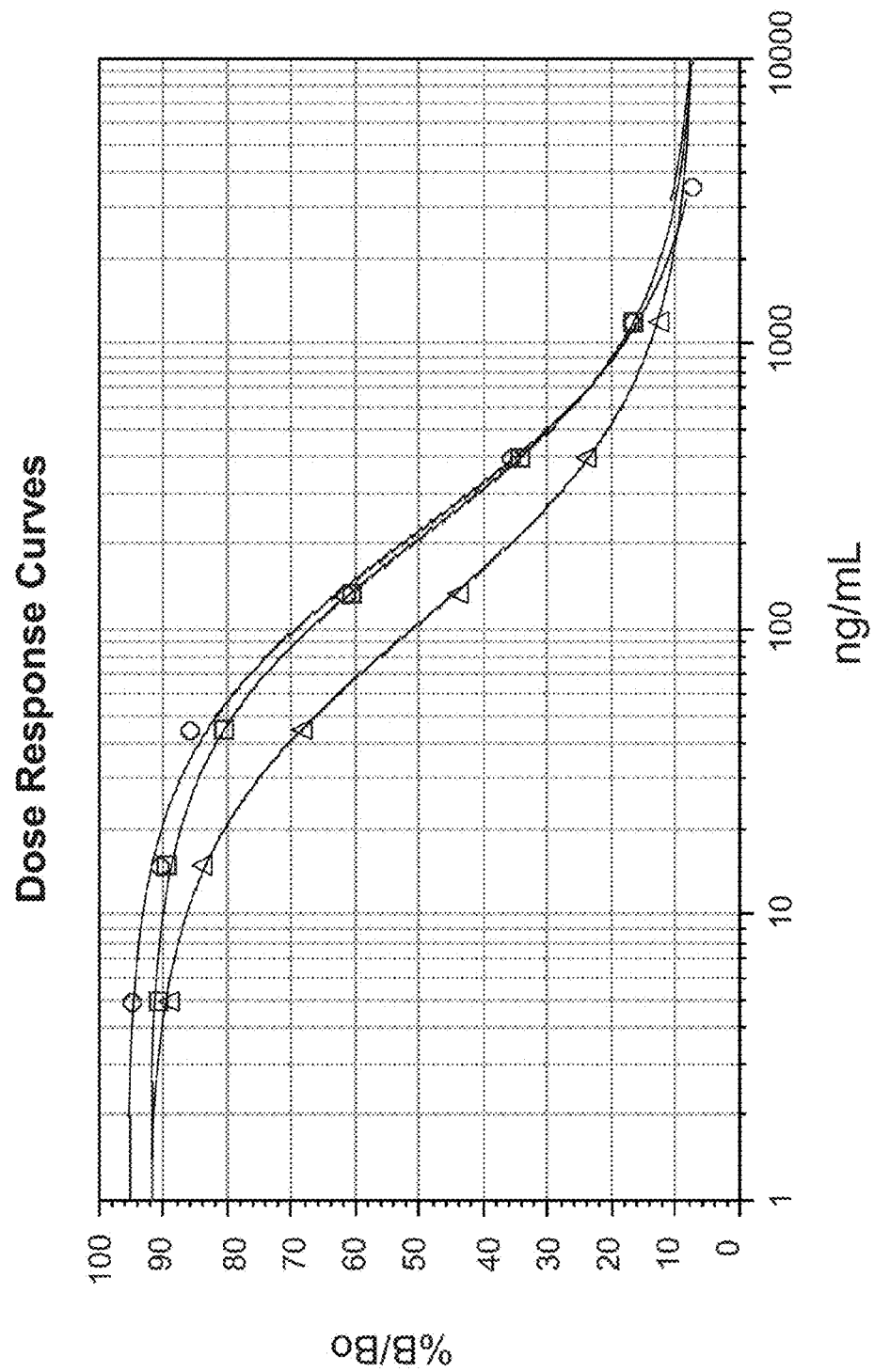

ANTI-TOFACITINIB ANTIBODIES AND USES THEREOF FOR DRUG MONITORING

CROSS-REFERENCE TO RELATED APPLICATIONS

This application is a national stage application under 35 U.S.C. §371 of International Application PCT/IB2013/055008, filed on Jun. 18, 2013, which claims priority to U.S. Provisional Patent Application No. 61/665,361, filed on Jun. 28, 2012, both of which are incorporated by reference herein in their entirety.

SEQUENCE LISTING

This application contains a Sequence Listing submitted as an electronic text file named "PC71701A_Sequence_Listing_ST25.txt", having a size in bytes of 18,000, and created on Dec. 24, 2014. The information contained in this electronic file is hereby incorporated by reference in its entirety.

FIELD OF THE INVENTION

This invention relates to antibodies specific to tofacitinib that selectively bind to tofacitinib over two known metabolites. The selectivity of the anti-tofacitinib antibodies makes them particularly useful for immunoassays. The invention further relates to immunoassays or kits that include antibodies specific for tofacitinib.

BACKGROUND

This invention relates to antibodies specific to tofacitinib, which are useful, e.g., in assay methods and assay kits for monitoring blood levels of the drug.

Tofacitinib is a potent immunosuppressant in development for the treatment of rheumatoid arthritis (RA), psoriasis, inflammatory bowel disease, and other immunological diseases, as well as for the prevention of organ transplant rejection. Tofacitinib specifically inhibits Janus activated kinase 3 (JAK3), which has a pivotal role in cytokine signal transduction governing lymphocyte survival, proliferation, differentiation and apoptosis.

In certain circumstances, when organs such as kidney, heart, lung, bone marrow, and liver are transplanted in humans, the body will sometimes reject the transplanted tissue. One treatment of organ transplant rejection comprises suppression of the immune system in a controlled manner with immunosuppressant drugs such as tofacitinib. Immunosuppressant drugs are carefully administered to transplant recipients to prevent rejection of the foreign (i.e. non-self) tissue. Successful treatment with immunosuppressant drugs requires the measurement of drug concentrations, followed by subsequent dosage adjustments to maximize efficacy while minimizing toxicity. Monitoring blood levels of tofacitinib in patients treated with tofacitinib is thus very desirable in order to regulate the dosage. The appropriate dosage will maintain the minimum drug activity level sufficient for pharmacologic activity while avoiding any undue risk of side effects. Thus, need exists for a sensitive and reliable assay for measuring tofacitinib levels in patients that can be performed quickly and easily in a clinical setting as part of the development of tofacitinib as a pharmaceutical.

To support the use of tofacitinib in the clinical setting, particularly for use in the prevention of organ transplant rejection, a long-felt need exists for monitoring plasma levels of tofacitinib in many patients to ensure that therapeutic levels are maintained, as well as to guide adjustment of dosages in a timely fashion as needed. This activity is often referred to as Therapeutic Drug Monitoring (TDM). TDM plays a key role in helping clinicians maintain blood and plasma levels of immunosuppressive drugs within their respective therapeutic ranges. Variation in concentrations outside of the narrow therapeutic ranges may result in adverse clinical outcomes. TDM ensures that concentrations of drug are not too high or too low, thereby reducing the risks of toxicity or rejection, respectively. Therapeutic monitoring of immunosuppressive drugs has generally been based on several choices of assay and biologic fluid (i.e., whole blood, plasma) appropriate for a particular drug.

A reliable liquid chromatography-mass spectrometry (LC-MS/MS) based assay is available for monitoring therapeutic levels of tofacitinib. Unfortunately, most clinical sites around the country and around the world are not set up to routinely perform LC-MS/MS assays in house. Clinical sites typically prefer relatively rapid, inexpensive, and easy to perform assays to streamline their TDM efforts. Accordingly, it would be advantageous to have immunoassays configured to detect tofacitinib in a patient's blood, serum, plasma, and/or other biological fluids or samples. Additionally, it would be advantageous to have tofacitinib-based immunogens for use in producing anti-tofacitinib antibodies.

Further, it would be advantageous to have specific anti-tofacitinib antibodies that bind tofacitinib but do not substantially bind at least one metabolite of tofacitinib. Such antibodies would be useful, among other things, to detect clinically relevant concentrations of tofacitinib in a sample from a patient undergoing therapy wherein tofacitinib is administered to the patient.

There have been no previous reports of monoclonal antibodies which recognize tofacitinib. There are inherent difficulties in making monoclonal antibodies to tofacitinib because tofacitinib is not immunogenic and is itself immunosuppressive. Moreover, as the metabolites of tofacitinib have not been well characterized in the literature, it is difficult to identify a monoclonal antibody capable of differentiating between tofacitinib and its metabolites. A need exists for an accurate assay to detect active tofacitinib but not its inactive metabolites. The present invention meets that need.

BRIEF SUMMARY OF THE INVENTION

The present invention is directed to novel immunogenic tofacitinib conjugates, as well as labeled tofacitinib competitors. The present invention is also directed to polyclonal and monoclonal antibodies generated using the immunogenic tofacitinib conjugates. These antibodies, conjugates, and competitors are useful in, among other things, immunoassays for the detection of tofacitinib in a sample.

The present invention includes an immunogenic tofacitinib conjugate comprising tofacitinib coupled to an immunogenic carrier, wherein the immunogenic carrier is a protein selected from the group consisting of keyhole limpet hemocyanin and bovine serum albumin, and further wherein (a) the immunogenic tofacitinib conjugate has the structure

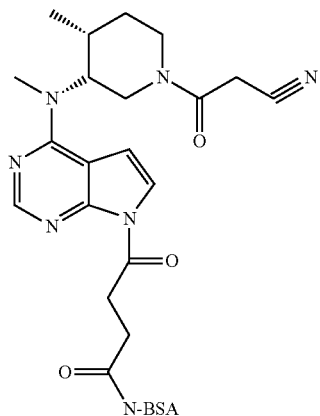

Formula V wherein BSA is bovine serum albumin; or
(b) the immunogenic tofacitinib conjugate has the structure

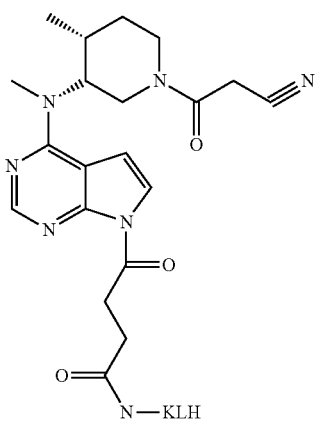

Formula VI wherein KLH is keyhole limpet hemocyanin.

The invention includes a method for assessing the concentration of tofacitinib in a sample. The method comprises:
(a) providing a sample suspected of containing tofacitinib;
(b) contacting the sample or sample extract with an antibody specific for tofacitinib under conditions suitable for binding of the antibody to tofacitinib to form an assay mixture; and
(c) detecting binding of the antibody to tofacitinib.

The invention includes an isolated antibody having greater binding affinity for tofacitinib than for tofacitinib metabolite 1 of Formula II and tofacitinib metabolite 2 of Formula III

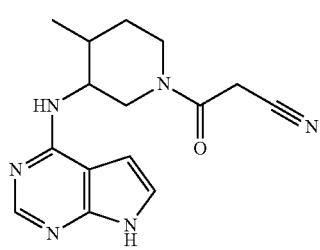

Formula II

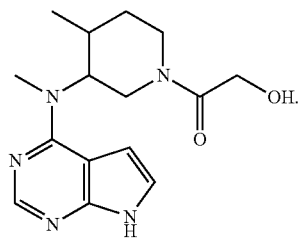

Formula III

In one aspect, the isolated antibody has a binding affinity for tofacitinib that is 25, 30, 40, or 50 times the binding affinity for metabolite 1 or metabolite 2.

In another aspect, the antibody is obtained using an immunogenic tofacitinib conjugate compound comprising tofacitinib coupled to an immunogenic carrier.

The invention includes a method of determining the amount of tofacitinib in a sample. The method comprises:
providing known amount of a labeled competitor comprising tofacitinib coupled to a detectable label;
providing a selective anti-tofacitinib antibody;
combining the sample, the selective anti-tofacitinib antibody and the labeled competitor, wherein the tofacitinib in the sample competes with the labeled competitor for binding to the selective anti-tofacitinib antibody; and
determining the amount of tofacitinib in the sample by measuring the amount of labeled competitor not bound to antibody by detection of the label.

In one aspect, the selective anti-tofacitinib antibody has a greater binding affinity for tofacitinib than for tofacitinib metabolite 1 of Formula II

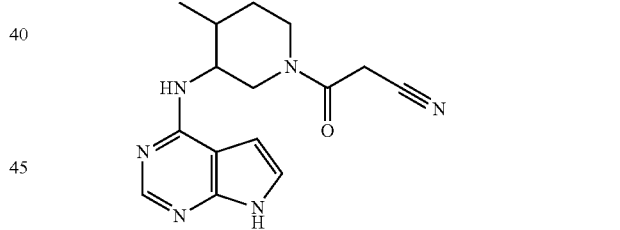

Formula II and/or for tofacitinib than for tofacitinib metabolite 2 of Formula III

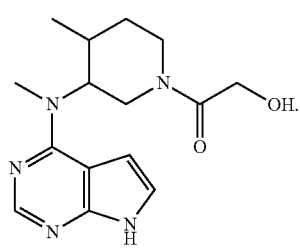

Formula III

In one aspect, the antibody has greater binding affinity for tofacitinib than for tofacitinib metabolite 1 of Formula II and tofacitinib metabolite 2 of Formula III

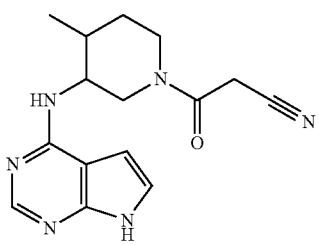

Formula II

The invention includes a kit for determining the amount of tofacitinib in a sample.

The kit comprises:

a labeled competitor comprising tofacitinib coupled to a detectable label; and at least one selective anti-tofacitinib antibody; wherein the labeled competitor competes with the tofacitinib in a sample for binding to the anti-tofacitinib antibody.

In one aspect, the selective anti-tofacitinib antibody has a greater binding affinity for tofacitinib than for at least one tofacitinib metabolite selected from the group consisting of tofacitinib metabolite 1 of Formula II

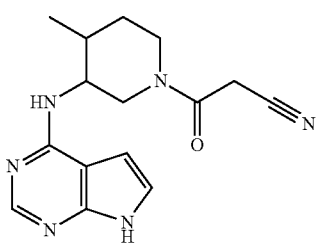

Formula II and tofacitinib metabolite 2 of Formula III

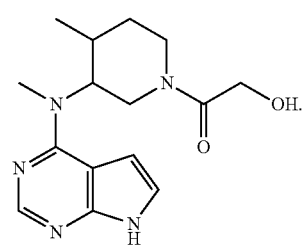

Formula III

In another aspect, the antibody has greater binding affinity for tofacitinib than for tofacitinib metabolite 1 of Formula II and tofacitinib metabolite 2 of Formula III In another aspect, the kit can be used to detect tofacitinib in a sample at a concentration ranging from about 5 ng/ml to about 1215 ng/ml and comprises (a) an antibody comprising a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24; and/or (b) an antibody comprising a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;

The invention includes a competitive immunoassay kit for determining the concentration of tofacitinib in a sample. The competitive immunoassay comprises: at least one selective anti-tofacitinib antibody; a tofacitinib compound conjugated to a detectable label; wherein the conjugated tofacitinib compound competes with the tofacitinib in the sample to bind with the antibody; and wherein the label provides a signal indicative of the concentration of tofacitinib in the sample when the tofacitinib in the sample is present in a therapeutic drug monitoring concentration.

In one aspect, the antibody has greater binding affinity for tofacitinib than for tofacitinib metabolite 1 of Formula II and tofacitinib metabolite 2 of Formula III -continued

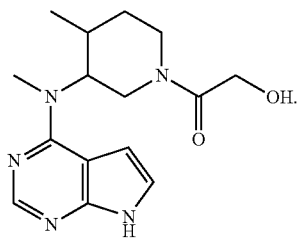

Formula III

The invention includes an isolated antibody that binds to tofacitinib but does not substantially bind to at least one tofacitinib metabolite selected from the group consisting of a tofacitinib metabolite 1 of Formula II and a tofacitinib metabolite 2 of Formula III

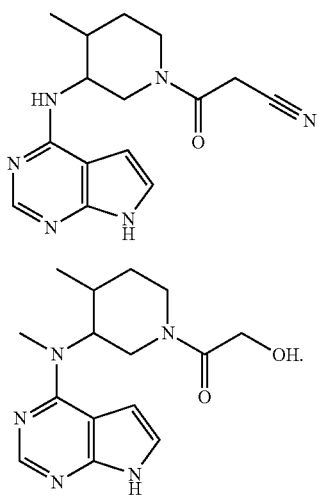

Formula II

Formula III

In one aspect, the isolated antibody does not substantially bind a tofacitinib metabolite 1 of Formula II and a tofacitinib metabolite 2 of Formula III

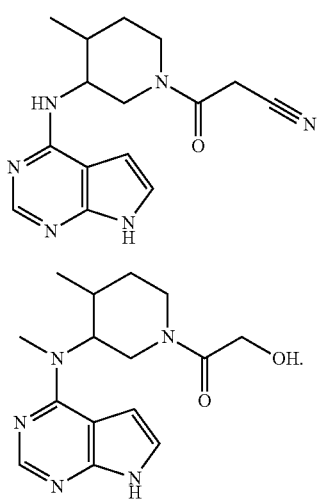

Formula II

Formula III

In another aspect, the antibody can detect tofacitinib in a sample but not substantially detect a tofacitinib metabolite in the sample, and wherein the amount of tofacitinib ranges from about 5 ng/mL to 1215 ng/mL, from about 5 ng/mL to 405 ng/mL, or about 15 ng/mL to 1215 ng/mL.

The invention includes an isolated antibody having greater binding affinity for tofacitinib than for at least one tofacitinib metabolite selected from the group consisting of a tofacitinib metabolite 1 of Formula II and a tofacitinib metabolite 2 of Formula III. The antibody comprises a heavy chain variable domain and a light chain variable domain, wherein the heavy chain variable domain comprises three complementarity determining regions (HCDR1, HCDR2, and HCDR3) selected from the group consisting of:
  (a) a HCDR1 comprising an amino acid sequence selected from the group consisting of SEQ ID NO:13, SEQ ID NO:19, SEQ ID NO:30, and SEQ ID NO:37;
  (b) a HCDR2 comprising an amino acid sequence selected from the group consisting of SEQ ID NO:14, SEQ ID NO:20, SEQ ID NO:25, SEQ ID NO:31, and SEQ ID NO:38;
  (c) a HCDR3 comprising an amino acid sequence selected from the group consisting of SEQ ID NO:15, SEQ ID NO:21, SEQ ID NO:26, SEQ ID NO:32, and SEQ ID NO:39; and wherein the light chain variable domain comprises three CDRs (LCDR1, LCDR2, and LCDR3) selected from the group consisting of:
  (d) a LCDR1 comprising an amino acid sequence selected from the group consisting of SEQ ID NO:16, SEQ ID NO:22, SEQ ID NO:27, SEQ ID NO:33, and SEQ ID NO:34;
  (e) a LCDR2 comprising an amino acid sequence selected from the group consisting of SEQ ID NO:17, SEQ ID NO:23, SEQ ID NO:28, and SEQ ID NO:35; and
  (f) a LCDR3 comprising an amino acid sequence selected from the group consisting of SEQ ID NO:18, SEQ ID NO:24, SEQ ID NO:29, and SEQ ID NO:34.

In one aspect, the antibody comprises
  (a) a HCDR1 comprising the amino acid sequence of SEQ ID NO:13, a HCDR2 comprising the amino acid sequence of SEQ ID NO:14, a HCDR3 comprising the amino acid sequence of SEQ ID NO:15, and further comprising a LCDR1 comprising the amino acid sequence of SEQ ID NO:16, a LCDR2 comprising the amino acid sequence of SEQ ID NO:17, and a LCDR3 comprising the amino acid sequence of SEQ ID NO:18;
  (b) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
  (c) a HCDR1 comprising the amino acid sequence of SEQ ID NO:19, a HCDR2 comprising the amino acid sequence of SEQ ID NO:25, a HCDR3 comprising the amino acid sequence of SEQ ID NO:26, and further comprising a LCDR1 comprising the amino acid sequence of SEQ ID NO:27, a LCDR2 comprising the amino acid sequence of SEQ ID NO:28, and a LCDR3 comprising the amino acid sequence of SEQ ID NO:29;
  (d) a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(e) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:33, a LCDR2 comprising the amino acid sequence of SEQ ID NO:17, and a LCDR3 comprising the amino acid sequence of SEQ ID NO:18;
(f) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:34, a LCDR2 comprising the amino acid sequence of SEQ ID NO:35, and a LCDR3 comprising the amino acid sequence of SEQ ID NO:36;
(g) a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(h) a heavy chain variable domain comprising an amino acid sequence selected from the group consisting of SEQ ID NO:1, SEQ ID NO:3, SEQ ID NO:5, SEQ ID NO:7, SEQ ID NO:8, SEQ ID NO:10 and SEQ ID NO:12, and further comprising a light chain variable domain comprising an amino acid sequence selected from the group consisting of SEQ ID NO:2, SEQ ID NO:4, SEQ ID NO:6, SEQ ID NO:9, and SEQ ID NO:11;
(i) a heavy chain variable domain comprising the amino acid sequence of SEQ ID NO:1 and a light chain variable domain comprising the amino acid sequence of SEQ ID NO:2;
(j) a heavy chain variable domain comprising the amino acid sequence of SEQ ID NO:3 and a light chain variable domain comprising the amino acid sequence of SEQ ID NO:4;
(k) a heavy chain variable domain comprising the amino acid sequence of SEQ ID NO:7 and a light chain variable domain comprising the amino acid sequence of SEQ ID NO:4;
(l) a heavy chain variable domain comprising the amino acid sequence of SEQ ID NO:12 and a light chain variable domain comprising the amino acid sequence of SEQ ID NO:4;
(m) a heavy chain variable domain comprising the amino acid sequence of SEQ ID NO:5 and a light chain variable domain comprising the amino acid sequence of SEQ ID NO:6;
(n) a heavy chain variable domain comprising the amino acid sequence of SEQ ID NO:8 and a light chain variable domain comprising the amino acid sequence of SEQ ID NO:9;
(o) a heavy chain variable domain comprising the amino acid sequence of SEQ ID NO:10 and a light chain variable domain comprising the amino acid sequence of SEQ ID NO:11;
(p) a heavy chain variable domain comprising an amino acid sequence selected from the group consisting of SEQ ID NO3, SEQ ID NO:7 and SEQ ID NO:12 and a light chain variable domain comprising the amino acid sequence of SEQ ID NO:4; and
(q) a heavy chain variable domain comprising an amino acid sequence selected from the group consisting of SEQ ID NO:3, SEQ ID NO:8, SEQ ID NO:10, and SEQ ID NO:12 and a light chain variable domain comprising an amino acid sequence selected from the group consisting of SEQ ID NO:4, SEQ ID NO:9 and SEQ ID NO:11.

In another aspect, the antibody is selected from the group consisting of:
(a) an antibody comprising a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24:
(b) an antibody comprising a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(c) an antibody comprising a heavy chain variable domain comprising an amino acid sequence selected from the group consisting of SEQ ID NO:3, SEQ ID NO:7 and SEQ ID NO:12 and further comprising a light chain variable domain comprising the amino acid sequence of SEQ ID NO:4;
(d) an antibody comprising a heavy chain variable domain comprising the amino acid sequence of SEQ ID NO:7 and further comprising a light chain variable domain comprising the amino acid sequence of SEQ ID NO:4; and
(e) an antibody comprising a heavy chain variable domain comprising the amino acid sequence of SEQ ID NO:12 and further comprising a light chain variable domain comprising the amino acid sequence of SEQ ID NO:4.

In one aspect, the antibody is capable of detecting tofacitinib in a sample at a concentration ranging from about 15 ng/ml to 1215 ng/ml.

In another aspect, the antibody is capable of detecting tofacitinib in a sample at a concentration ranging from about 5 ng/ml to 405 ng/ml.

In yet another aspect,
The invention includes a nucleic acid encoding an antibody comprising
(a) a HCDR1 comprising the amino acid sequence of SEQ ID NO:13, a HCDR2 comprising the amino acid sequence of SEQ ID NO:14, a HCDR3 comprising the amino acid sequence of SEQ ID NO:15, and further comprising a LCDR1 comprising the amino acid sequence of SEQ ID NO:16, a LCDR2 comprising the amino acid sequence of SEQ ID NO:17, and a LCDR3 comprising the amino acid sequence of SEQ ID NO:18;
(b) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(c) a HCDR1 comprising the amino acid sequence of SEQ ID NO:19, a HCDR2 comprising the amino acid sequence of SEQ ID NO:25, a HCDR3 comprising the amino acid sequence of SEQ ID NO:26, and further comprising a LCDR1 comprising the amino acid sequence of SEQ ID NO:27, a LCDR2 comprising the amino acid sequence of SEQ ID NO:28, and a LCDR3 comprising the amino acid sequence of SEQ ID NO:29;
(d) a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(e) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:33, a LCDR2 comprising the amino acid sequence of SEQ ID NO:17, and a LCDR3 comprising the amino acid sequence of SEQ ID NO:18;
(f) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:34, a LCDR2 comprising the amino acid sequence of SEQ ID NO:35, and a LCDR3 comprising the amino acid sequence of SEQ ID NO:36;
(g) a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;
(h) a heavy chain variable domain comprising an amino acid sequence selected from the group consisting of SEQ ID NO:1, SEQ ID NO:3, SEQ ID NO:5, SEQ ID NO:7, SEQ ID NO:8, SEQ ID NO:10 and SEQ ID NO:12, and further comprising a light chain variable domain comprising an amino acid sequence selected from the group consisting of SEQ ID NO:2, SEQ ID NO:4, SEQ ID NO:6, SEQ ID NO:9, and SEQ ID NO:11;
(i) a heavy chain variable domain comprising the amino acid sequence of SEQ ID NO:1 and a light chain variable domain comprising the amino acid sequence of SEQ ID NO:2;
(j) a heavy chain variable domain comprising the amino acid sequence of SEQ ID NO:3 and a light chain variable domain comprising the amino acid sequence of SEQ ID NO:4;
(k) a heavy chain variable domain comprising the amino acid sequence of SEQ ID NO:7 and a light chain variable domain comprising the amino acid sequence of SEQ ID NO:4;
(l) a heavy chain variable domain comprising the amino acid sequence of SEQ ID NO:12 and a light chain variable domain comprising the amino acid sequence of SEQ ID NO:4;
(m) a heavy chain variable domain comprising the amino acid sequence of SEQ ID NO:5 and a light chain variable domain comprising the amino acid sequence of SEQ ID NO:6;
(n) a heavy chain variable domain comprising the amino acid sequence of SEQ ID NO:8 and a light chain variable domain comprising the amino acid sequence of SEQ ID NO:9;
(o) a heavy chain variable domain comprising the amino acid sequence of SEQ ID NO:10 and a light chain variable domain comprising the amino acid sequence of SEQ ID NO:11;
(p) a heavy chain variable domain comprising an amino acid sequence selected from the group consisting of SEQ ID NO3, SEQ ID NO:7 and SEQ ID NO:12 and a light chain variable domain comprising the amino acid sequence of SEQ ID NO:4; and
(q) a heavy chain variable domain comprising an amino acid sequence selected from the group consisting of SEQ ID NO:3, SEQ ID NO:8, SEQ ID NO:10, and SEQ ID NO:12 and a light chain variable domain comprising an amino acid sequence selected from the group consisting of SEQ ID NO:4, SEQ ID NO:9 and SEQ ID NO:11.

In one aspect, the invention includes a host cell comprising the nucleic acid.

In another aspect, the invention includes a method of producing the antibody. The method comprises culturing the host cell under conditions wherein the antibody is produced. In a further aspect, the method comprises isolating the antibody.

BRIEF DESCRIPTION OF THE DRAWINGS

The disclosed subject matter is particularly pointed out and distinctly claimed in the claims at the conclusion of the specification. The foregoing and other objects, features, and advantages of the disclosed embodiments are apparent from the following detailed description taken in conjunction with the accompanying drawings in which:

FIG. 5 is a graph depicting optimal dilution ranges of select monoclonal antibodies of the invention as determined by ELISA.

DETAILED DESCRIPTION OF THE INVENTION

Figure 1:
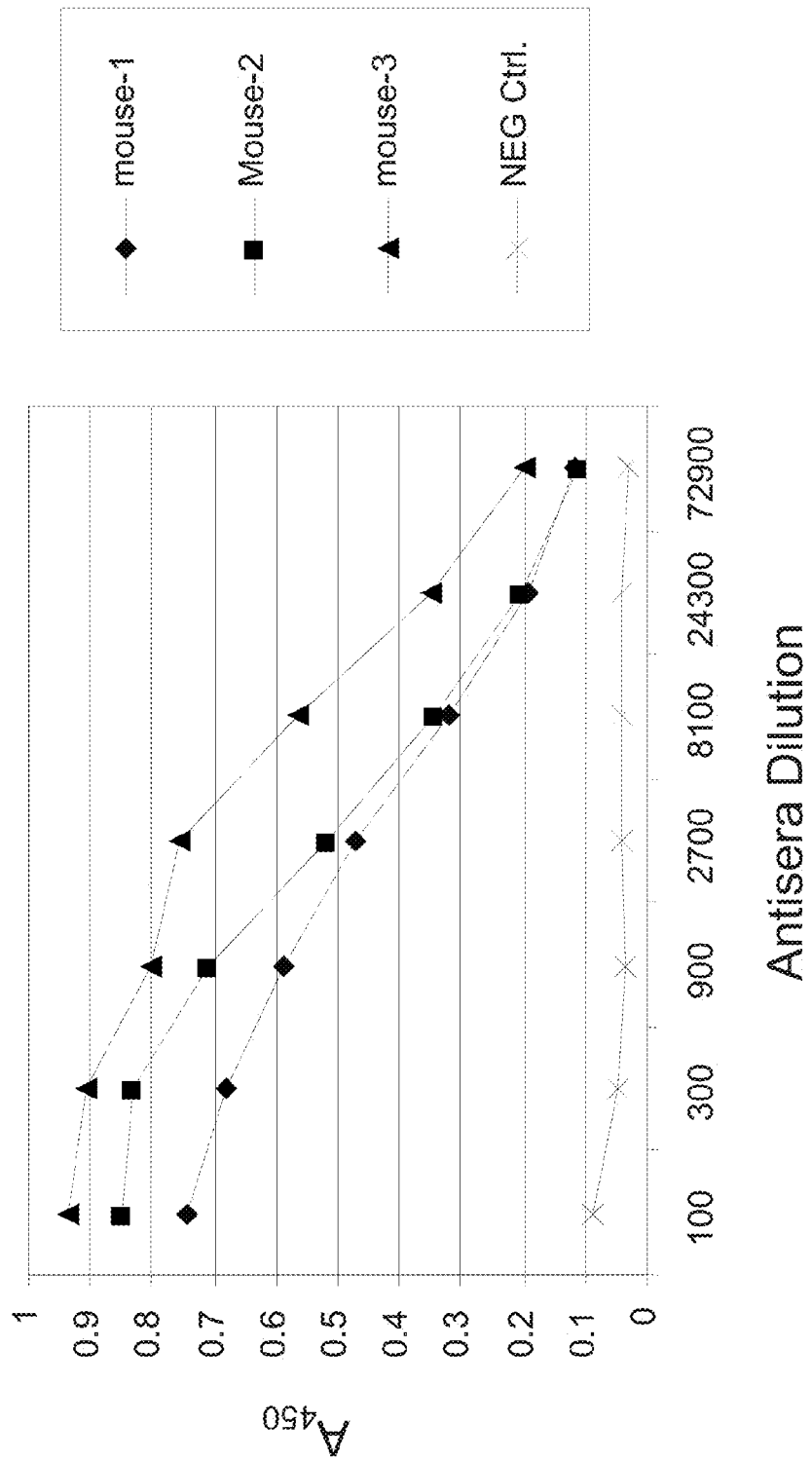
FIG. 1 is a graph depicting binding of serum antibodies to the tofacitinib-BSA conjugate of example 2 as determined by solid phase ELISA.

The present invention provides novel immunogenic tofacitinib conjugates comprising tofacitinib coupled to an immunogenic carrier, as well as labeled tofacitinib competitors. The present invention is also directed to polyclonal and monoclonal antibodies generated using the immunogenic tofacitinib conjugates.

The present invention also provides polyclonal and monoclonal antibodies which are specific for tofacitinib. In some embodiments, the antibodies of the invention are produced in response to inoculation with a novel immunogenic tofacitinib conjugate comprising tofacitinib linked to an immunogenic carrier.

These antibodies, conjugates, and competitors are useful in immunoassays for the detection of tofacitinib in biological fluids. Assay kits comprising these antibodies, conjugates and competitors are well suited for use in a clinical setting and provide far more accurate and reproducible results than was previously possible. The antibodies are also useful in the purification and isolation of tofacitinib.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. An "antibody" also refers to an IgA, IgD, IgE, IgG, IgM antibody subtype. Each heavy chain is comprised of a heavy chain variable region (abbreviated herein as $V_H$) and a heavy chain constant region ($C_H$). The heavy chain constant region is typically comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "IMGT definition" (Lefranc, M.-P. et al., 1999, Nucleic Acids Res. 27:209-212) and the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol. 262:732-745. In another approach, referred to herein as the "conformational definition" of CDRs, the positions of the CDRs may be identified as the residues that make enthalpic contributions to antigen binding. See, e.g., Makabe et al., 2008, J. Biol. Chem. 283: 1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "antigen-binding portion" or "antigen-binding fragment" of an antibody (or simply "antibody portion"), as used herein, refers to one or more fragments of an antibody that retain the ability to specifically bind to an antigen (e.g., tofacitinib). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., 1989, Nature 341:544-546), which consists of a $V_H$ domain; and (vi) an isolated complementarity determining region. Furthermore, although the two domains of the Fv fragment, Wand $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988, Science 242:423-426; and Huston et al., 1988, Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds tofacitinib is substantially free of antibodies that specifically bind antigens other than tofacitinib). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "recombinant antibody", as used herein, includes all antibodies that are prepared, expressed, created or isolated by recombinant means, such as (a) antibodies isolated from a host cell transformed to express the antibody, (b) antibodies isolated from a recombinant, combinatorial antibody library, and (c) antibodies prepared, expressed, created or isolated by any other means that involve splicing of immunoglobulin gene sequences to other DNA sequences. Such recombinant antibodies comprise variable regions in which the framework and CDR regions are derived from mouse germline immunoglobulin sequences. In certain embodiments, however, such recombinant mouse antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to mouse germline $V_H$ and $V_L$ sequences, may not naturally exist within the mouse antibody germline repertoire in vivo.

As used herein, "isotype" refers to the antibody class (e.g., IgM or IgG) that is encoded by the heavy chain constant region genes.

The phrases "an antibody recognizing an antigen" and "an antibody specific for an antigen" are used interchangeably herein with the term "an antibody which binds specifically to an antigen."

The term "antibody derivatives" refers to any modified form of the antibody, e.g., a conjugate of the antibody and another agent or antibody.

The term "humanized antibody" is intended to refer to antibodies in which CDR sequences derived from the germline of a non-human species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. Chimeric antibody can also include an antibody where the V domain and C domain are each derived two different sources even if both are from the same species.

As used herein, an antibody that "specifically binds to tofacitinib" or "a selective tofacitinib antibody" refers to an antibody that binds to tofacitinib but which does not substantially bind a metabolite of tofacitinib. An antibody specifically binds tofacitinib where it does not detectably binds to a tofacitinib metabolite 1 of Formula II and/or to a tofacitinib metabolite 2 of Formula III or binds to such metabolite to a much lesser extent. For instance, the metabolite does not substantially compete with tofacitinib for binding to the antibody as measured by, for example, a competitive binding assay. A selective tofacitinib antibody binds to tofacitinib with an affinity that is 5, 10, 15, 25, 30, 40, or 50 times greater than its affinity to metabolite 1 of Formula II or metabolite 2 of Formula III.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

Various aspects of the invention are described in further detail in the following subsections.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196(4): 901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "IMGT definition" (Lefranc, M.-P. et al., Nucleic Acids Res., 27, 209-212 (1999)) and the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "monoclonal antibody" (Mab) refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

Antibodies of the invention can be produced using techniques well known in the art, e.g., recombinant technologies, phage display technologies, synthetic technologies or combinations of such technologies or other technologies readily known in the art (see, for example, Jayasena, S. D., 1999, Clin. Chem. 45:1628-1650 and Fellouse et al., 2007, J. Mol. Biol., 373(4):924-940).

The terms "specific binding," "selective binding" "selectively binds," or "specifically binds" as used herein refer to the ability to bind to a target compound or epitope with greater affinity than to a non-target compound. In an illustrative example, an antibody that specifically binds tofacitinib has a greater affinity for tofacitinib than for metabolites of tofacitinib, e.g., metabolite 1 of Formula II and metabolite 2 of Formula III. In some embodiments, "specifically binds" or "selectively binds" refers to binding to a target compound with an affinity that is at least 5, 10, 15, 20, 25, 30, 50, 100, 500, 1000 or more times greater than the affinity for a non-target.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds.

As used herein, the terms "immunogen" and "immunogenic" are meant to refer to substances capable of producing or generating an immune response in an organism. An immunogen can also be antigen. Usually, an immunogen has a fairly high molecular weight (e.g., greater than 10,000), thus, a variety of macromolecules such as proteins, lipoproteins, polysaccharides, some nucleic acids, and certain of the teichoic acids, can be an immunogen.

"Haptens" are partial or incomplete antigens. They are usually protein-free substances, mostly of low molecular weight, which are not generally capable of stimulating antibody formation, but which do react with antibodies. Antibodies to a hapten may be generated by coupling a hapten to a high molecular weight antigenic carrier (e.g., an immunogen) and then injecting this coupled product, i.e., an immunogenic conjugate, into a human or animal subject. For example, tofacitinib is a hapten.

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles, and nucleic acid that are recognized as foreign and thereby elicit an immunologic response from the host. Various proteins may be employed as a polypeptide immunogenic carrier. These proteins include albumins and serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic polypeptides may be used. The immunogenic carrier can also be a polysaccharide such as, e.g., starches, glycogen, cellulose, carbohydrate gums such as gum arabic, agar, and so forth. The polysaccharide can also contain polypeptide residues and/or lipid residues. The immunogenic carrier can also be a polynucleotide either alone or conjugated to one of the polypeptides or polysaccharides mentioned above.

As used herein, the term "immunogenicity" is meant to refer to the ability of a molecule to induce an immune response, which may be determined both by the intrinsic chemical structure of the injected molecule and by whether or not the host animal's immune system recognizes the compound. Small changes in the structure of an antigen can greatly alter the immunogenicity of a compound, and have been used extensively as a general procedure to increase the chances of raising an antibody, particularly against well-conserved antigens. For example, these modification techniques either alter regions of the immunogen to provide better sites for T-cell binding or expose new epitopes for B-cell binding.

As used herein the term "label" refers to any molecule that produces, or can be induced to produce, a detectable signal. The label can be conjugated to an analyte, an immunogen, and/or an antibody. Non-limiting examples of labels include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, and hapten radioactive isotopes.

The term "labeled," with regard to a specific antibody or a labeled competitor, includes direct labeling by coupling (i.e., physically linking) a detectable substance to the antibody or labeled competitor, as well as indirect labeling of the antibody or labeled competitor by coupling it with another reagent that is, in turn, directly labeled. An example of indirect labeling includes detection of a primary antibody using a fluorescent-labeled secondary antibody. In vitro techniques for detection of an antigen of the invention include enzyme linked immunosorbent assays (ELISAs), Western blots, immunoprecipitation, and immunofluorescence.

The antibodies, labeled competitors, and potential therapeutic compounds described herein are also suitable for use with any of a number of other homogeneous and heterogeneous immunoassays with a range of detection systems.

As used herein, the term "antigenic compound" refers to a compound used to produce an immune response. Illustratively, the antigenic compound is a hapten, for example tofacitinib, linked to an immunogenic carrier. The antigenic compound is used to generate the desired antibodies.

The term "labeled competitor" as used herein is a molecule capable of specific binding to antibodies having specificity for tofacitinib, wherein the molecule is linked to a detectable label or tracer. Illustratively, the molecule is tofacitinib or a derivative or analyte thereof.

The term "biological sample" includes, but is not limited to, any quantity of a substance isolated or derived from a living subject or formerly living subject. The term is intended to include tissues, cells, and biological fluids isolated from a subject, as well as tissues, cells, and fluids present within a subject. Subjects include, but are not limited to, chicken, humans, mice, monkeys, rats, rabbits, horses, camelids, and other animals. Such substance include, but are not limited to, blood, plasma, serum, semen, urine, tears, saliva, cells, organs, tissues, bone, bone marrow, lymph, lymph nodes, synovial tissue or fluid, chondrocytes, synovial macrophages, endothelial cells, and skin.

In one aspect, this disclosure provides derivatives of tofacitinib which are useful as immunogenic molecules for the generation of antibodies specific for tofacitinib for measuring levels of tofacitinib.

In another aspect, this disclosure provides methods and kits for selectively detecting tofacitinib in a sample.

Tofacitinib (Formula I) is an orally available, potent selective inhibitor of JAK3 that is in development for the treatment of rheumatoid arthritis (RA) and other autoimmune disorders, such as inflammatory bowel disease, ankylosing spondylitis, psoriasis, psoriatic arthritis, and the prevention of transplant rejection.

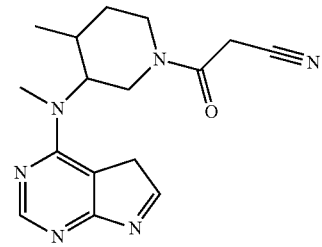

Formula I

Tofacitinib has at least two known metabolites, "metabolite I" (Formula II) and "metabolite II" (Formula III).

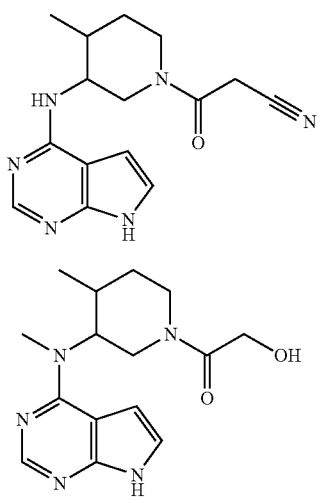

Formula II

Formula III

Implementing an immunoassay for the detection of a small molecule, such as tofacitinib, can be difficult. In some cases, small molecules lack antigenicity, making it difficult to generate antibodies against them. This challenge is compounded for tofacitinib because it has such potent immunosuppressive properties. To increase the immunogenicity of small molecules, larger immunogenic compounds, including but not limited to bovine serum albumin, ovalbumin, keyhole limpet hemocyanin, and the like, can be coupled to the drug. Detection of the drug in a sample generally requires the use of a detectable label conjugated to an antibody, tofacitinib, or tofacitinib analog.

Prior to the present invention, it was not expected that tofacitinib could be rendered more immunogenic by conjugation to an immunogenic carrier. Thus, surprisingly, in one aspect, this disclosure provides an immunogenic tofacitinib conjugate comprising tofacitinib coupled to an immunogenic carrier, wherein the immunogenic carrier is a protein, glycoprotein, complex polysaccharide, or nucleic acid that is recognized by the immunized animal as foreign, resulting in an immunologic response. In one illustrative example, the immunogenic carrier is a protein selected from the group consisting of keyhole limpet hemocyanin (KLH) and bovine serum albumin (BSA).

In one embodiment, this disclosure provides an immunogenic tofacitinib conjugate of formula V, having the structure

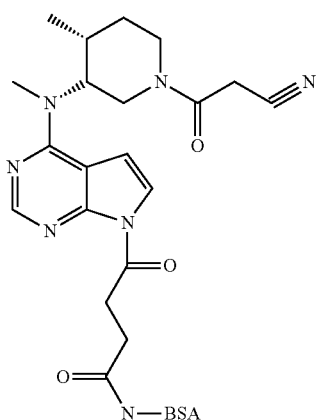

Formula V wherein BSA is bovine serum albumin.

In another embodiment, this disclosure provides an immunogenic tofacitinib conjugate of formula VI, having the structure

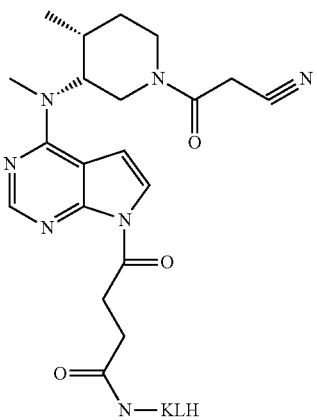

Formula VI wherein KLH is Keyhole Limpet Hemocyanin.

The immunogenic tofacitinib conjugates of the present invention can be used to elicit antibodies using known antibody producing and screening procedures. The immunogenic tofacitinib conjugates can be injected into appropriate animal hosts to stimulate the production of antibodies. The antibodies so produced can be harvested for direct use in immunoassays configured to detect tofacitinib. In some cases, it is desirable to have a monoclonal antibody that is specific to tofacitinib, and which selectively binds to tofacitinib over tofacitinib metabolites. In some embodiments, the antibody has a binding affinity for tofacitinib that is about 25, 30, 40, or 50 times the binding affinity for metabolite 1 or metabolite 2. In some embodiments, the antibody binds to metabolite 1 or metabolite 2 with an affinity that is less than about 5%, 4%, 3%, 2%, 1%, or 0.5% of the binding affinity to tofacitinib.

Selective Anti-Tofacitinib Antibodies

The antibodies of the present invention are characterized by the fact that they bind specifically to tofacitinib (Formula I), but which do not substantially bind to one or both known tofacitinib metabolites, "metabolite 1 of Formula II" and "metabolite 2 of Formula III," and methods of making and using these anti-tofacitinib antibodies. A selective tofacitinib antibody binds to tofacitinib with an affinity that is 5, 10, 15, 25, 30, 40, or 50 times greater than its affinity to metabolite 1 of Formula II or metabolite 2 of Formula III.

Standard assays to evaluate the binding ability of the antibodies toward tofacitinib and its metabolites are known in the art, including for example, ELISAs, Western blots, radioimmunoassays, and flow cytometry analysis. Suitable assays are described in detail in the Examples. The binding kinetics (e.g., binding affinity) of the antibodies also can be assessed by standard assays known in the art, such as by Biacore SPR analysis and Octet analysis.

The antibodies of the invention include mouse monoclonal antibodies 5A3.E5, 10A6.C5, 10F10.H5, 6D9.A5, 12H4.G2, 16F10.E6, and 12D4.G6. The $V_H$ amino acid sequences of 5A3.E5, 10A6.C5, 10F10.H5, 6D9.A5, 12H4.G2, 16F10.E6, and 12D4.G6 are shown in Table 2, and are set forth in SEQ ID NOs: 1, 3, 5, 7, 8, 10 and 12, respectively. The $V_L$ amino acid sequences of 5A3.E5, 10A6.C5, 10F10.H5, 6D9.A5, 12H4.G2, 16F10.E6, and 12D4.G6 are shown in Table 2 and are set forth in SEQ ID NOs: 2, 4, 6, 4, 9, 11 and 4, respectively.

The V$_H$ and V$_L$ sequences may be "mixed and matched" to create other selective tofacitinib binding molecules of the invention. Tofacitinib binding of such mixed and matched antibodies, as well as the binding of the antibody to one or both metabolites 1 and 2, can be tested using the binding assays described above and in the Examples. Optionally, when V$_H$ and V$_L$ chains are mixed and matched, a V$_H$ sequence from a particular V$_H$/V$_L$ pairing is replaced with a structurally similar V$_H$ sequence. Likewise, optionally a V$_L$ sequence from a particular V$_H$/V$_L$ pairing is replaced with a structurally similar V$_L$ sequence.

Accordingly, in one aspect, the invention provides an isolated monoclonal antibody, or antigen binding portion thereof, comprising:
  (a) a heavy chain variable domain comprising an amino acid sequence selected from the group consisting of SEQ ID NO:1, SEQ ID NO:3, SEQ ID NO:5, SEQ ID NO:7, SEQ ID NO:8, SEQ ID NO:10 and SEQ ID NO:12, and further comprising a light chain variable domain comprising an amino acid sequence selected from the group consisting of SEQ ID NO:2, SEQ ID NO:4, SEQ ID NO:6, SEQ ID NO:9, and SEQ ID NO:11;
  (b) a heavy chain variable domain comprising the amino acid sequence of SEQ ID NO:1 and a light chain variable domain comprising the amino acid sequence of SEQ ID NO:2;
  (c) a heavy chain variable domain comprising the amino acid sequence of SEQ ID NO:3 and a light chain variable domain comprising the amino acid sequence of SEQ ID NO:4;
  (d) a heavy chain variable domain comprising the amino acid sequence of SEQ ID NO:7 and a light chain variable domain comprising the amino acid sequence of SEQ ID NO:4;
  (e) a heavy chain variable domain comprising the amino acid sequence of SEQ ID NO:12 and a light chain variable domain comprising the amino acid sequence of SEQ ID NO:4;
  (f) a heavy chain variable domain comprising the amino acid sequence of SEQ ID NO:5 and a light chain variable domain comprising the amino acid sequence of SEQ ID NO:6;
  (g) a heavy chain variable domain comprising the amino acid sequence of SEQ ID NO:8 and a light chain variable domain comprising the amino acid sequence of SEQ ID NO:9;
  (h) a heavy chain variable domain comprising the amino acid sequence of SEQ ID NO:10 and a light chain variable domain comprising the amino acid sequence of SEQ ID NO:11;
  (i) a heavy chain variable domain comprising an amino acid sequence selected from the group consisting of SEQ ID NO3, SEQ ID NO:7 and SEQ ID NO:12 and a light chain variable domain comprising the amino acid sequence of SEQ ID NO:4; and
  (j) a heavy chain variable domain comprising an amino acid sequence selected from the group consisting of SEQ ID NO:3, SEQ ID NO:8, SEQ ID NO:10, and SEQ ID NO:12 and a light chain variable domain comprising an amino acid sequence selected from the group consisting of SEQ ID NO:4, SEQ ID NO:9 and SEQ ID NO:11.

In another aspect, the invention provides antibodies that comprise the heavy chain and/or light chain CDR1s, CDR2s and CDR3s of 5A3.E5, 10A6.C5, 10F10.H5, 6D9.A5, 12H4.G2, 16F10.E6, and 12D4.G6, or combinations thereof. The amino acid sequences of the V$_H$ CDR1s of 5A3.E5, 10A6.C5, 10F10.H5, 6D9.A5, 12H4.G2, 16F10.E6, and 12D4.G6 are shown in SEQ ID NOs: 13, 19, 19, 30, 19, 19, and 37, respectively. The amino acid sequences of the V$_H$ CDR2s of 5A3.E5, 10A6.C5, 10F10.H5, 6D9.A5, 12H4.G2, 16F10.E6, and 12D4.G6 are shown in SEQ ID NOs: 14, 20, 25, 31, 20, 20, and 38, respectively. The amino acid sequences of the V$_H$ CDR3s of 5A3.E5, 10A6.C5, 10F10.H5, 6D9.A5, 12H4.G2, 16F10.E6, and 12D4.G6 are shown in SEQ ID NOs:15, 21, 26, 32, 21, 21, and 39, respectively. The amino acid sequences of the V$_L$ CDR1s of 5A3.E5, 10A6.C5, 10F10.H5, 6D9.A5, 12H4.G2, 16F10.E6, and 12D4.G6 are shown in SEQ ID NOs:16, 22, 27, 22, 33, 34, and 22, respectively. The amino acid sequences of the V$_L$ CDR2s of 5A3.E5, 10A6.C5, 10F10.H5, 6D9.A5, 12H4.G2, 16F10.E6, and 12D4.G6 are shown in SEQ ID NOs:17, 23, 28, 23, 17, 35 and 23, respectively. The amino acid sequences of the V$_L$ CDR3s of 5A3.E5, 10A6.C5, 10F10.H5, 6D9.A5, 12H4.G2, 16F10.E6, and 12D4.G6 are shown in SEQ ID NOs:18, 24, 29, 24, 18, 36, and 24, respectively. The CDR regions are delineated using the Kabat system (Kabat, E. A., et al. Sequences of Proteins of Immunological Interest, Fifth Edition, U.S. Department of Health and Human Services, NIH Publication No. 91-3242 (1991)).

The heavy and light chain CDRs for the antibody 5A3.E5 comprise SEQ ID NOs: 13, 14, 15, 16, 17, 18. The heavy and light chain CDRs for the antibody 10A6.C5 comprise SEQ ID NOs: 19, 20, 21, 22, 23, and 24. The heavy and light chain CDRs for the antibody 10F10.H5 comprise SEQ ID NOs:19, 25, 26, 27, 28, and 29. The heavy and light chain CDRs for the antibody 6D9.A5 comprise SEQ ID NOs:30, 31, 32, 22, 23, and 24. The heavy and light chain CDRs for the antibody 12H4.G2 comprise SEQ ID NOs:19, 20, 21, 33, 17, and 18. The heavy and light chain CDRs for the antibody 16F10.E6 comprise SEQ ID NOs:19, 20, 21, 34, 35, and 36. The heavy and light chain CDRs for the antibody 12D4.G6 comprise SEQ ID NOs:37, 38, 39, 22, 23, and 24.

In yet another embodiment, an antibody of the invention comprises heavy and light chain variable regions and/or heavy chain and light chain CDR1 s, CDR2s and CDR3s comprising amino acid sequences that are homologous to the amino acid sequences of the antibodies previously described herein, and wherein the antibodies retain the desired functional properties of the selective anti-tofacitinib antibodies of the invention.

In various embodiments, the antibody can be, for example, a mouse antibody, a humanized antibody or a chimeric antibody derived from a mouse anti-tofacitinib antibody. In other embodiments, the V$_H$ and/or V$_L$ amino acid sequences may be 85%, 90%, 95%, 96%, 97%, 98% or 99% homologous to the sequences set forth above. As used herein, the percent homology between two amino acid sequences is equivalent to the percent identity between the two sequences. The percent identity between the two sequences is a function of the number of identical positions shared by the sequences, taking into account the number of gaps, and the length of each gap, which need to be introduced for optimal alignment of the two sequences.

In certain embodiments, an antibody of the invention comprises heavy and light chain variable regions and/or heavy chain and light chain CDR1s, CDR2s and CDR3s, wherein one or more of these sequences comprise specified amino acid sequences based on the antibodies described herein, or conservative modifications thereof, and wherein the antibodies retain the desired functional properties of the anti-tofacitinib antibodies of the invention.

In alternative embodiments, the antibody can be, for example, mouse antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

In another embodiment, the invention provides an antibody that binds to the same epitope on tofacitinib as the anti-tofacitinib antibodies of the invention (i.e., an antibody that has the ability to compete for binding to tofacitinib with an antibody of the invention). In alternative embodiments, the reference antibody for competition studies can be the monoclonal antibody 5A3.E5, 10A6.C5, 10F10.H5, 6D9.A5, 12H4.G2, 16F10.E6, and 12D4.G6. Such competing antibodies can be identified based on their ability to compete with 5A3.E5, 10A6.C5, 10F10.H5, 6D9.A5, 12H4.G2, 16F10.E6, or 12D4.G6 for binding of tofacitinib in standard binding assays. For example, Biacore analysis, Octect analysis, ELISA assays or flow cytometry may be used to demonstrate cross-competition with the antibodies of the current invention. The ability of a test antibody to inhibit the binding of, for example, 5A3.E5, 10A6.C5, 10F10.H5, 6D9.A5, 12H4.G2, 16F10.E6, or 12D4.G6, to tofacitinib, wherein the test antibody does not substantially bind metabolite 1 and/or metabolite 2, demonstrates that the test antibody can compete with 5A3.E5, 10A6.C5, 10F10.H5, 6D9.A5, 12H4.G2, 16F10.E6, and 12D4.G6 for binding to tofacitinib and thus may bind the same epitope on tofacitinib as 5A3.E5, 10A6.C5, 10F10.H5, 6D9.A5, 12H4.G2, 16F10.E6, and 12D4.G6. In a further embodiment, the antibody that binds to the same epitope on tofacitinib as 5A3.E5, 10A6.C5, 10F10.H5, 6D9.A5, 12H4.G2, 16F10.E6, and 12D4.G6 is a mouse monoclonal antibody. Such monoclonal antibodies can be prepared and isolated as described in the Examples or by a wide variety of methods well-known in the art. In other embodiments, the antibody that competes with the antibody is a human, humanized or mouse antibody.

An antibody of the invention can be prepared using an antibody comprising at least one of the $V_H$ and/or $V_L$ sequence disclosed herein as starting material to engineer a modified antibody, which may have properties that differ from the starting antibody but which may bind the same, or substantially the same, epitope as the starting material antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

The present invention provides nucleic acids encoding the tofacitinib specific antibody of the invention. Nucleic acids encoding the antibodies of the invention can be generated by methods known in the art. Also, as would be understood by one skilled in the art, due to the degeneracy of the nucleic acid code, a wide variety of nucleic acid sequences can encode the amino acid sequence of the antibody of the invention.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., 1998, Nature 332:323-327; Jones et al., 1986, Nature 321:522-525; Queen et al., 1989, Proc. Natl. Acad. See. U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 13, 19, 30, and 37; SEQ ID NOs:14, 20, 25, 31, and 38; and SEQ ID NOs:15, 21, 26, 32, and 39, respectively, and a light chain variable region comprising CDR1, CDR2, and CDR3 sequences comprising an amino acid sequence selected from the group consisting of SEQ ID NOs:16, 22, 27, 33, and 34; SEQ ID NOs: 17, 23, 28, and 35; and SEQ ID NOs:18, 24, 29, and 36, respectively. Such antibodies contain the $V_H$ and $V_L$ CDR sequences of monoclonal antibodies 5A3.E5, 10A6.C5, 10F10.H5, 6D9.A5, 12H4.G2, 16F10.E6, and 12D4.G6, which may contain a different framework sequence from the antibodies. Such framework sequences can be obtained from public DNA databases or published references that include germline antibody gene sequences.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Optionally, conservative modifications (as discussed above) are introduced. The mutations may be amino acid substitutions, additions or deletions. Moreover, typically no more than one, two, three, four or five residues within a CDR region are altered.

In yet another embodiment, the invention provides isolated anti-phospho-tau monoclonal antibodies, or antigen binding portions thereof, comprising a heavy chain variable region comprising:

(a) a $V_H$ CDR1 region comprising an amino acid sequence selected from the group consisting of SEQ ID NOs:13, 19, 30, and 37, or an amino acid sequence having one, two, three, four or five amino acid substitutions, deletions or additions as compared to SEQ ID NOs: 13, 19, 30, and 37; (b) a $V_H$ CDR2 region comprising an amino acid sequence selected from the group consisting of SEQ ID NOs: 14, 20, 25, 31, and 38, or an amino acid sequence having one, two, three, four or five amino acid substitutions, deletions or additions as compared to SEQ ID NOs: 14, 20, 25, 31, and 38; (c) a $V_H$ CDR3 region comprising an amino acid sequence selected from the group consisting of SEQ ID NOs: 15, 21, 26, 32, and 39, or an amino acid sequence having one, two, three, four or five amino acid substitutions, deletions or additions as compared to SEQ ID NOs: 15, 21, 26, 32, and 39; (d) a $V_L$ CDR1 region comprising an amino acid sequence selected from the group consisting of SEQ ID NOs: 16, 22, 27, 33, and 34, or an amino acid sequence having one, two, three, four or five amino acid substitutions, deletions or additions as compared to SEQ ID NOs: 16, 22, 27, 33, and 34; (e) a $V_L$ CDR2 region comprising an amino acid sequence selected from the group consisting of SEQ ID NOs: 17, 23, 28, and 35, or an amino acid sequence having one, two, three, four or five amino acid substitutions, deletions or additions as compared to SEQ ID NOs: 17, 23, 28, and 35; and (f) a $V_L$ CDR3 region comprising an amino acid sequence selected from the group consisting of SEQ ID NOs: 18, 24, 29, and 36, or an amino acid sequence having one, two, three, four or five amino acid substitutions, deletions or additions as compared to SEQ ID NOs: 18, 24, 29, and 36.

Engineered antibodies of the invention include those in which modifications have been made to framework residues within $V_H$ and/or $V_L$, e.g., to improve the properties of the antibody. Typically such framework modifications are made to decrease the immunogenicity of the antibody. For example, one approach is to "backmutate" one or more framework residues to the corresponding germline sequence (also referred to as "germlining"). More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 2003/0153043. In addition to, or alternative to, modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polymers including polyethylene glycol (PEG), such as a reactive ester or aldehyde derivative of PEG, under conditions in which one or more PEG groups become attached to the antibody or antibody fragment. Alternatively, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention.

Methods of Engineering Antibodies

As discussed above, the selective anti-tofacitinib antibodies having $V_H$ and $V_L$ sequences disclosed herein can be used to create new anti-tofacitinib antibodies by modifying the $V_H$ and/or $V_L$ sequences, or the constant region(s) attached thereto. Thus, in another aspect of the invention, the structural features of an anti-tofacitinib antibody of the invention are used to create structurally related anti-tofacitinib antibodies that retain at least one functional property of the antibodies of the invention, such as binding to tofacitinib but not substantially binding to metabolite 1 and/or metabolite 2. For example, one or more CDR regions of 5A3.E5, 10A6.C5, 10F10.H5, 6D9.A5, 12H4.G2, 16F10.E6, and/or 12D4.G6, or mutations thereof, can be combined recombinantly with known framework regions and/or other CDRs to create additional, recombinantly-engineered, anti-tofacitinib antibodies, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Standard molecular biology techniques can be used to prepare and express the altered antibody sequence.

Optionally, the antibody encoded by the altered antibody sequence(s) is one that retains one, some, or all of the functional properties of the anti-tofacitinib antibodies described herein, which functional properties include, but are not limited to:
  (i) does not substantially bind to tofacitinib metabolite 1 of Formula II; and/or
  (ii) does not substantially bind to tofacitinib metabolite 2 of Formula III.

The functional properties of the altered antibodies can be assessed using standard assays available in the art and/or described herein, as well as those known in the art or those discovered in the future.

In certain embodiments of the methods of engineering antibodies of the invention, mutations can be introduced randomly or selectively along all or part of an anti-tofacitinib antibody coding sequence and the resulting modified anti-tofacitinib antibodies can be screened for binding activity and/or other functional properties as described herein. Mutational methods are well-known in the art.

Production of Monoclonal Antibodies of the Invention

Monoclonal antibodies (mAbs) of the present invention can be produced by a variety of techniques, including conventional monoclonal antibody methodology. Mouse, rat, rabbit, camelid and human monoclonal antibodies of the invention can also be prepared using phage display methods for screening libraries of immunoglobulin genes from those, or many other, species. Such phage display methods for isolating antibodies are established in the art and encompass phage display libraries prepared from immunized animals or humans or naïve phage display libraries where the original starting material is not derived from immunized animals. Phage display is well known in the art and is described, for example, in U.S. Pat. No. 5,223,409, WO 91/17271, WO92/20791; and WO 92/15679.

The monoclonal antibodies of the invention can also be prepared by culturing a host cell comprising a nucleic acid encoding the monoclonal antibody under suitable conditions and recovering said antibody, or antigen binding portion thereof. Such host cell culturing methods are well-known in the art.

Methods of Use

This disclosure further provides a method for assessing the presence or concentration of tofacitinib in a sample, the method comprising providing a sample suspected of containing tofacitinib; contacting the sample or sample extract with an antibody specific for tofacitinib under conditions suitable for binding of the antibody to tofacitinib to form an assay mixture; and detecting binding of the antibody to tofacitinib.

In another embodiment, this disclosure provides a method of determining the concentration of tofacitinib in a sample. The method comprises providing a labeled competitor comprising tofacitinib coupled to a detectable label; providing a selective anti-tofacitinib antibody that binds to tofacitinib but not to metabolites 1 and/or 2; combining the sample, the selective anti-tofacitinib antibody, and the labeled competitor, wherein the tofacitinib in the sample competes with the labeled competitor for binding to the selective anti-tofacitinib antibody; and determining the concentration of tofacitinib in the sample by measuring the amount of the labeled competitor not bound to the antibody by detection of the label. In an exemplary embodiment, the amount of labeled competitor (tofacitinib) is detected in a sample that does not contain tofacitinib and the amount of label detected in the sample is compared to the amount of label present where tofacitinib may be present. The difference between the amount of label detected in the absence of tofacitinib and the amount of label in the sample that is suspected of containing tofacitinib is measured.

In another embodiment, this disclosure provides competitive immunoassay kits for determining the presence or absence of tofacitinib in a sample are provided. Illustrative competitive immunoassay kits, such as an enzyme linked immunoassay (ELISA), comprise an antibody capable of specifically binding tofacitinib, and a tofacitinib compound conjugated to a detectable label, wherein the conjugated tofacitinib compound is configured to compete with the tofacitinib in the sample to bind with the antibody, and wherein the label provides a signal indicative of a concentration of tofacitinib in the sample when the tofacitinib in the sample is present in therapeutic drug monitoring concentrations.

In one embodiment, this disclosure provides a competitive immunoassay for determining the presence of tofacitinib in a sample at a concentration of drug within the therapeutic range of tofacitinib. However, it is understood that it may be useful to provide information across a broader range, and the immunoassay range is generally broader than the therapeutic range. Accordingly, immunoassays that monitor therapeutic drug concentrations may provide sensitivity across a broader range of tofacitinib concentrations. In one aspect, the competitive immunoassays are suitable for monitoring the presence of tofacitinib in a sample at a concentration in the range of about 0 to about 1500 ng/ml. In another aspect, the competitive immunoassays are suitable for monitoring the presence of tofacitinib in a sample at a concentration in the range of about 5 to about 1215 ng/ml. In another aspect, the competitive immunoassays are suitable for monitoring the presence of tofacitinib in a sample at a concentration in the range of about 5 to about 500 ng/ml. In another aspect, the competitive immunoassays are suitable for monitoring the presence of tofacitinib in a sample at a concentration in the range of about 5 to about 405 ng/ml. In another aspect, the competitive immunoassays are suitable for monitoring the presence of tofacitinib in a sample at a concentration in the range of about 15 to about 1215 ng/ml.

In one competitive immunoassay, the labeled competitor may be derived from tofacitinib using a linkage that is the same or similar to that of the immunogenic tofacitinib conjugate. In some competitive immunoassays, it is desirable to have a labeled competitor that binds to the anti-tofacitinib antibody with less specificity than tofacitinib binds to the anti-tofacitinib antibody, allowing for the labeled competitor to be displaced more readily in the presence of tofacitinib.

The antibodies, immunogenic tofacitinib conjugates, labeled competitors and/or other conjugates described herein are also suitable for use with any of a number of other homogeneous and heterogeneous immunoassays with a range of detection systems. The examples presented herein are not intended to be limiting.

Thus, the present invention provides tofacitinib conjugates that are useful for the preparation of immunogens and conjugates for use in immunoassays for the detection of tofacitinib. By coupling a tofacitinib analog according to the present invention to an immunogenic carrier material, polyclonal or monoclonal antibodies can be produced and isolated, which are useful reagents for immunoassays for the detection of tofacitinib. Coupling can be accomplished by any chemical reaction that will bind the label or carrier.

Illustrative tofacitinib immunoassays employ anti-tofacitinib antibodies that can be either polyclonal or monoclonal. In illustrative competitive immunoassays, the antibody preparation used is induced by an immunogen described herein is formulated in an aqueous solution such as buffer, and the like or provided in an adjuvant or similar composition. The induced antibodies can be tested to determine specificity for tofacitinib.

The antibodies and labeled competitors described herein are also suitable for use with any of a number of other homogeneous and heterogeneous immunoassays with a range of detection systems.

Kits

The invention provides a kit for determining the concentration of tofacitinib in a sample, the kit comprising at least one selective anti-tofacitinib antibody. In one aspect, the kit further comprises a labeled competitor comprising tofacitinib coupled to a detectable label. In another embodiment, the labeled competitor competes with the tofacitinib in a sample for binding to the anti-tofacitinib antibody. In another aspect, the selective anti-tofacitinib antibody is produced using an immunogenic tofacitinib conjugate comprising tofacitinib coupled to an immunogenic carrier. The kit may also include an applicator and/or instructional material for the use of the kit.

In another embodiment, the invention includes a kit for determining the concentration of tofacitinib in a sample wherein the kit comprises at least one selective tofacitinib antibody that binds tofacitinib but does not substantially bind at least one metabolite selected from the group consisting of tofacitinib metabolite 1 of Formula II and tofacitinib metabolite 2 of Formula III. In one aspect, the kit comprises at least one selective tofacitinib antibody that binds tofacitinib but does not substantially bind tofacitinib metabolite 1 of Formula II and does not substantially bind tofacitinib metabolite 2 of Formula III. In one aspect, the kit further comprises an applicator. In another aspect, the kit comprises an instructional material for the use of the kit.

In one aspect, the kit can detect a concentration of tofacitinib ranging from 5 ng/ml to 1215 ng/ml. In another aspect, the kit can detect a concentration of tofacitinib ranging from 5 ng/ml to 405 ng/ml. In yet another aspect, the kit can detect a concentration of tofacitinib ranging from 15 ng/ml to 1215 ng/ml.

The present invention is further illustrated by the following examples which should not be construed as further limiting. The contents of all figures and all references, patents and published patent applications cited throughout this application are expressly incorporated herein by reference.

EXAMPLES

Example 1

Conjugation of Tofacitinib with Succinic Acid 40 mg succinic anhydride and 0.2 ml TEA (50 mM triethanolamine, 50 mM KCl, 20 mM MgCl$_2$, pH 7.5) were added to a solution of 47 mg of tofacitinib in 0.8 ml acetonitrile. The reaction mixture was shaken at a temperature of 60° C. for one hour. At one hour, an additional 50 mg succinic anhydride was added to the reaction mixture, followed by addition one incubation at 60° C. with shaking. Purified material was obtained following HPLC purification in a mobile phase gradient of 0-30% acetonitrile (ACNN) affording 25.2 mg of the tofacitinib hemisuccinate intermediate of Formula IV.

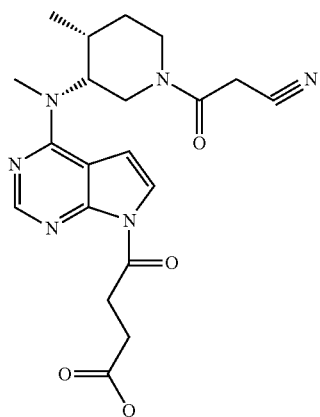

Formula IV

Example 2

Synthesis of an Immunogenic Tofacitinib Conjugate Comprising Tofacitinib Coupled to BSA 1.5 mg of the compound of Formula IV was dissolved in 2 ml 1-Ethyl-3-[3-dimethylamino-propyl]carbodiimide hydrochloride (EDC) conjugation buffer (0.1 M MES, 0.9 M NaCl, 0.02% NaN$_3$, pH 4.7). 8 mg BSA (Imject BSA obtained from Pierce #77601) was dissolved in 0.8 ml water and then mixed with the formula IV solution. Next, 10 mg EDC was dissolved in 0.1 ml H$_2$O and then immediately added to BSA, Formula IV mixture. The mixture was gently shaken for 2 hours at room temperature. The mixture was spun down and the supernatant containing the tofacitinib-BSA conjugate (Formula V) was purified by desalting according to standard desalting methods known to those of skill in the art. Conjugation of tofacitinib with BSA was confirmed by Matrix-Assisted Laser Desorption Ionization (MALDI).

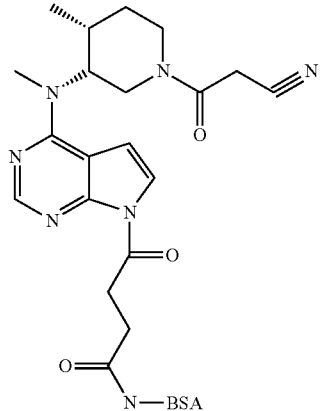

Formula V

Example 3

Synthesis of an Immunogenic Tofacitinib Conjugate Comprising Tofacitinib Coupled to BSA 1.5 mg of the compound of Formula IV was dissolved in 1.5 ml EDC conjugation buffer. 10 mg EDC was dissolved in 0.2 ml water and immediately added into Formula IV solution. The Formula IV/EDC mixture was added into 0.6 ml Mariculture Keyhole Limpet Hemocyanin (mcKLH, obtained from Pierce #77601) solution (10 mg/ml in water). The reaction mixture was gently shaken at room temperature for two hours. The mixture was spun down and the supernatant containing the tofacitinib-KLH conjugate (Formula VI) was purified by desalting according to standard desalting methods known to those of skill in the art.

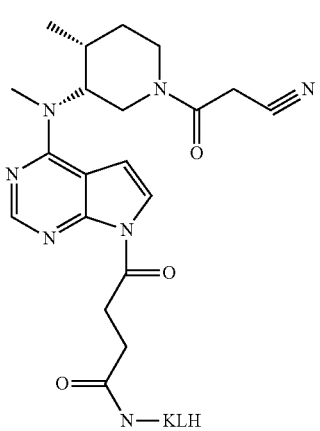

Formula VI

Example 4

Synthesis of a Tofacitinib Labeled Competitor

One illustrative example of a tofacitinib labeled competitor is a biotinylated tofacitinib derivative of Formula VII. The biotinylated tofacitinib derivative of Formula VII was produced as follows.

18 mg of the compound of Formula IV and 20 mg EDC were dissolved in 1 ml EDC conjugation buffer. 0.1 ml acetonitrile was added to help dissolve the compound. The pH of the solution was adjusted to 5.5 with addition of 10 µl 5 M NaOH. Then, 23 mg amine-PEG3-biotin was added. The mixture was shaken at room temperature overnight. Following the overnight incubation, biotinylated tofacitinib (Formula VII) was purified by HPLC in a mobile phase gradient of 0-30% ACN affording 14 mg of purified compound.

C., and washed 3× with washing buffer (PBS containing 0.5% (v/v) Tween 20). The antibody samples (i.e., the mouse serum or the hybridoma supernatants) to be screened were diluted in a diluent (0.1% solution of BSA in PBS). The diluted antibody samples were added to microtiter plate and the plate was incubated for 1-2 hours at room temperature. After having washed away any unbound substances with washing buffer, the level of bound anti-tofacitinib antibody was determined using rabbit or goat anti-mouse peroxidase-conjugated secondary antibody (IgG specific) at recommended or experimentally derived dilution (usually 1/1000-1/10,000) in the diluent. After incubation for 30 minutes at room temperature and 3× wash with washing buffer, the chromogenic substrate, OPD (o-phenylenediamine), was added, then color was developed for 20 minutes, and stopped by adding 50 µl 2 N sulfuric acid. Absorbance at 490 nm was measured. FIG. 1 is a graph depicting binding of serum antibodies to the tofaci-

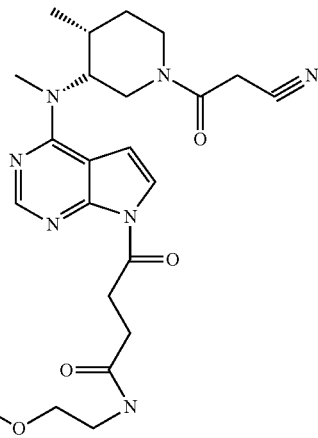

Formula VII

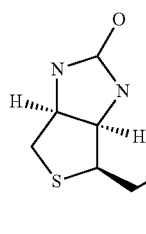

Example 5

Production of Anti-Tofacitinib Antibodies

Polyclonal and monoclonal antibodies were produced by using conventional techniques, essentially as described by Kohler and Milstein, Nature 256:495-497 (1975). Three female Balb/C mice were immunized with 100 µg of the immunogenic tofacitinib-KLH conjugate of example 3 in complete Freund's adjuvant, administered by intraperitoneal (ip) injection. Three subsequent injections were administered ip comprising 50 µg/mouse of the immunogenic tofacitinib-KLH conjugate in incomplete Freund's adjuvant on days 10, 20, and 30 after initial injection. Serum was collected on day 37 and the presence of antibodies reactive to the antigen was determined by solid phase ELISA, as described below, against immunogenic tofacitinib-BSA conjugate of example 2.

Solid Phase ELISA:

The immunogenic tofacitinib-BSA conjugate of example 2 was immobilized to wells of a microtiter plate. Specifically, microtiter plates were coated with 2-10 µg/ml tofacitinib-BSA conjugate in a coating buffer (0.2 M carbonate buffer (BuPH carbonate-bicarbonate buffer pack, Pierce item #28382) for 1-2 hours at room temperature or overnight at 4° C., then saturated with a blocking buffer (PBS containing 1% (w/v) BSA) for 1 hour at room temperature or overnight at 4° tinib-BSA conjugate of example 2 as determined by solid phase ELISA. As demonstrated in FIG. 1, antibodies reactive to the antigen were present in each of mouse 1, 2 and 3. As mouse 3 had the highest titer (defined as the dilution of serum at 50% maximum signal), this mouse was selected for hybridoma generation.

Hybridoma Generation:

The mouse demonstrating the highest serum antibody titer (defined as the dilution of serum at 50% maximum signal), mouse 3, received booster injection comprising 25 µg of antigen. Three days later, the mouse was sacrificed and its spleen cells were isolated and fused with NS1 myeloma cells following a standard fusion protocol. These mixtures of clones, called parental clones, were screened at 10 days after the fusion by solid-phase ELISA (described above) against immunogenic tofacitinib-BSA to identify parental clones that secreted antibodies capable of binding tofacitinib. Positive parental clones were selected for further analysis.

These positive parental clones originating from the fusion were expanded from the 96 well plates to 24 well plates and were rescreened 3 days later to ensure that the clones were still producing antibody. From the rescreen, selected wells with positive hybridomas, (i.e., hybridomas that secreted antibodies capable of binding the immunogenic tofacitinib-BSA conjugate and that did not bind to metabolite-1-BSA, metabolite-2-BSA) were frozen for future use and sub-cloned to isolate positive cell lines.

The selected positive parent clones that secreted antibodies capable of binding immunogenic tofacitinib-BSA conjugate were subcloned by limiting dilution to obtain monoclonal hybridoma cell lines. Approximately 10 days after subcloning, small volumes of media were removed from the wells and screened by solid-phase ELISA to identify antibody-producing clones. Selected positive clones were expanded and rescreened to ensure that the clones were still producing antibody and confirm specificity. Up to two positive clones per parental line, including clones 6D9.A5 and 12D4.G6, were expanded for freezing 2 vials each. 1 ml supernatant was also collected for testing.

In addition to the direct solid-phase ELISA described above in Example 5, alternative immunoassay formats were developed, including competitive a competitive immunoassay format for the detection of tofacitinib in experimental samples. Exemplary competitive immunoassay protocols are provided below.

Given that tofacitinib is a powerful immunosuppressant, the production of antibodies to tofacitinib was surprising. Even more surprising, was the exquisite selectivity of these antibodies in that, as shown below, they distinguished between tofacitinib and two metabolites thereof, selectively binding tofacitinib but not substantially binding either one or both metabolites.

Competitive Anti-tofacitinib Immunoassay-1

The direct solid-phase ELISA described above in Example 5 was converted to a competitive ELISA wherein a defined amount of monoclonal antibody replaced immune serum samples or hybridoma supernatants, a competitor (i.e., tofacitinib, tofacitinib metabolites) was then added to the monoclonal antibody solution, and binding of the monoclonal antibody to the tofacitinib-BSA conjugate in the presence and absence of the competitor was measured.

Competitive Anti-Tofacitinib Immunoassay-2

Microtiter plates were coated with 100 µl/well 1 µg/ml purified anti-tofacitinib antibody in a coating buffer for 3 hours at room temperature, then replaced with 300 µl/well blocking buffer (PBS containing 1% non-fat dry milk powder) for 30 minutes at room temperature, and washed 3× with washing buffer (PBS containing 0.5%) Tween 20). 100 µl/well of mixture biotinylated tofacitinib (0.03 µg/ml), an unlabeled competitor, such as tofacitinib (1.0-0.001 µg/ml), Metabolite 1 or Metabolite 2, and streptavidin-HRP (1:16, 000 dilution, may vary with lot) was added and incubated for 2 hours at room temperature. After 3× washing, 100 µl OPD substrate was added, then color was developed for 20 minutes, and the reaction was stopped by adding 50 µl 2 N sulfuric acid. Absorbance at 450 nm was measured.

Competitive Anti-Tofacitinib Immunoassay-3

200 µl/well of mixture containing anti-tofacitinib MAb (1/100 to 1/1638400 dilution), biotinylated tofacitinib (1 ng/ml), and a non-labeled competitor, such as tofacitinib (1000 to 0.001 ng/ml), Metabolite 1 (400-0.097 ng/ml) or Metabolite 2, was added into goat anti-mouse IgG pre-coated plates, and incubated for 1-2 hour at room temperature. After washing the plates, 200 µl of streptavidin-HRP (50 ng/ml) was added and the plates were then incubated for 0.5-1 hour at room temperature. After washing the plates again, 200 µl of TMB (3,3',5,5'-Tetramethylbenzidine) substrate was added, then color developed for 30 minutes, and the reaction was stopped by adding 50 µl 2 N sulfuric acid. Absorbance at 450 nm was measured.

Example 6

Binding of Anti-Tofacitinib Monoclonal Antibodies to Biotinylated Tofacitinib

Selected antibodies were further tested for binding to tofacitinib by standard ELISA. Briefly, a total of 34 clones were screened for binding to biotinylated tofacitinib. The format of the ELISA was as follows. Biotinylated tofacitinib (1 ng/mL) was incubated with antibody dilutions ranging from 1:100 to 1:1,638,400 on a pre-coated goat anti-mouse IgG plate for one hour. After having washed away any unbound substances, the binding of biotinylated tofacitinib to antibody was measured after the addition of streptavidin-HRP and the related chromogenic substrate TMB according to known methods.

Figure 2:
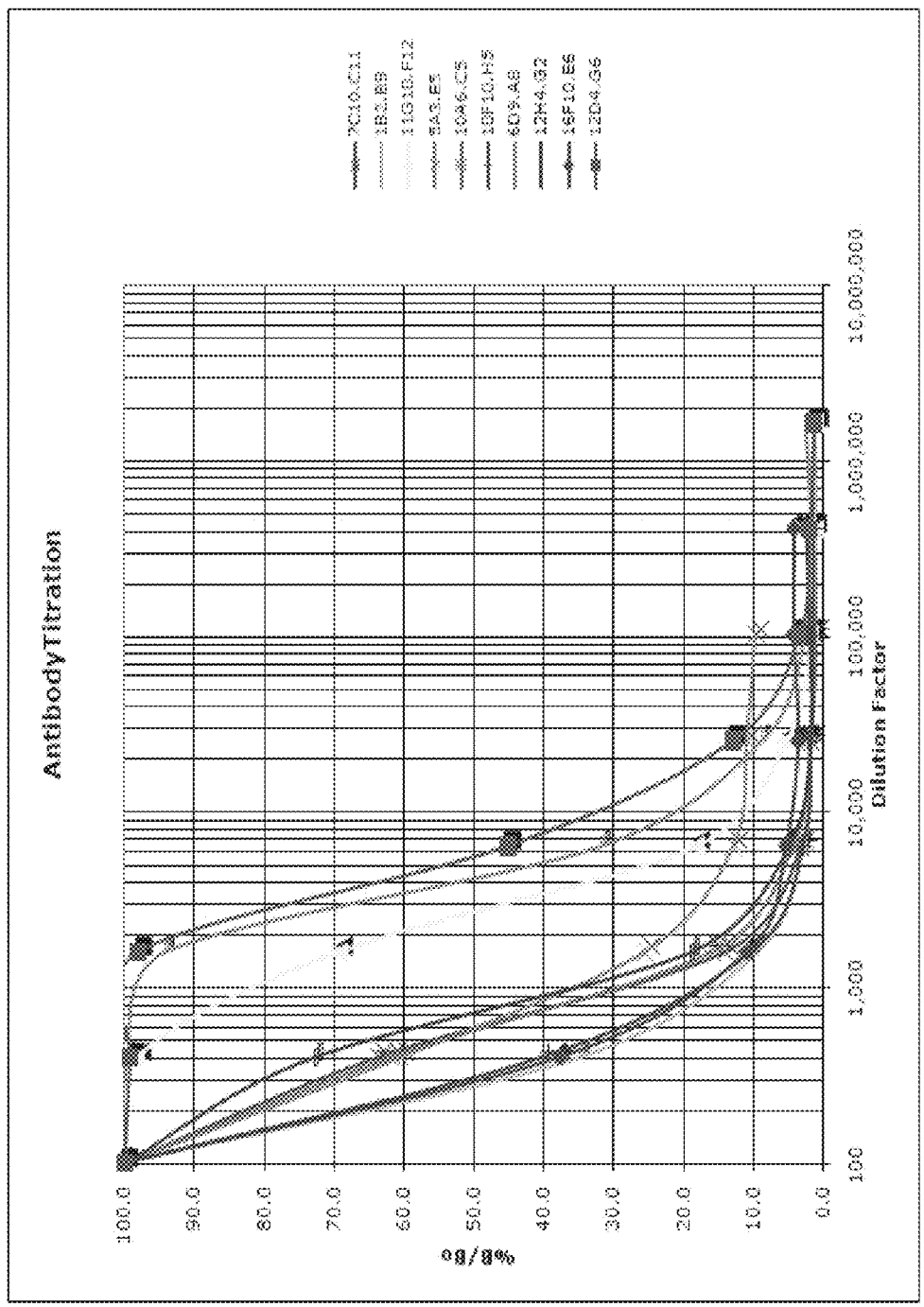
FIG. 2 is a graph depicting binding of selected anti-tofacitinib antibodies to biotinylated tofacitinib as determined by ELISA.

FIG. 2 is a graph depicting binding of selected anti-tofacitinib antibodies to biotinylated tofacitinib as determined by ELISA. Eleven antibodies were found to bind to biotinylated tofacitinib in a concentration dependent manner. Data for ten of these antibodies are shown in FIG. 2 and the data for antibody 8B5.F2 is not shown.

These eleven clones were selected for further analysis. Specifically, these eleven clones were evaluated for cross reactivity with the tofacitinib metabolite 1.

Example 7

Binding of Anti-Tofacitinib Monoclonal Antibodies to Metabolite 1

Antibodies were be further characterized as binding to tofacitinib or its metabolites by measuring cross reactivity using competitive immunoassay-3 mentioned above wherein tofacitinib metabolites as competitors.

For this example, eleven anti-tofacitinib monoclonal antibodies were screened for cross reactivity with metabolite 1 using competitive immunoassay. 200 µl/well of mixture containing anti-tofacitinib MAb (1/100 to 1/1638400 dilution), biotinylated tofacitinib (1 ng/ml), and Metabolite 1 (400-0.097 ng/ml), was added into goat anti-mouse IgG pre-coated plates, and incubated for 1-2 hour at room temperature. After washing the plates, 200 µl of streptavidin-HRP (50 ng/ml) was added and then incubated for 0.5-1 hour at room temperature. After washing the plates again, 200 µl of TMB substrate was added, then developed for 30 minutes, and stopped by adding 50 µl 2 N sulfuric acid. Absorbance at 450 nm was measured.

Figure 3:
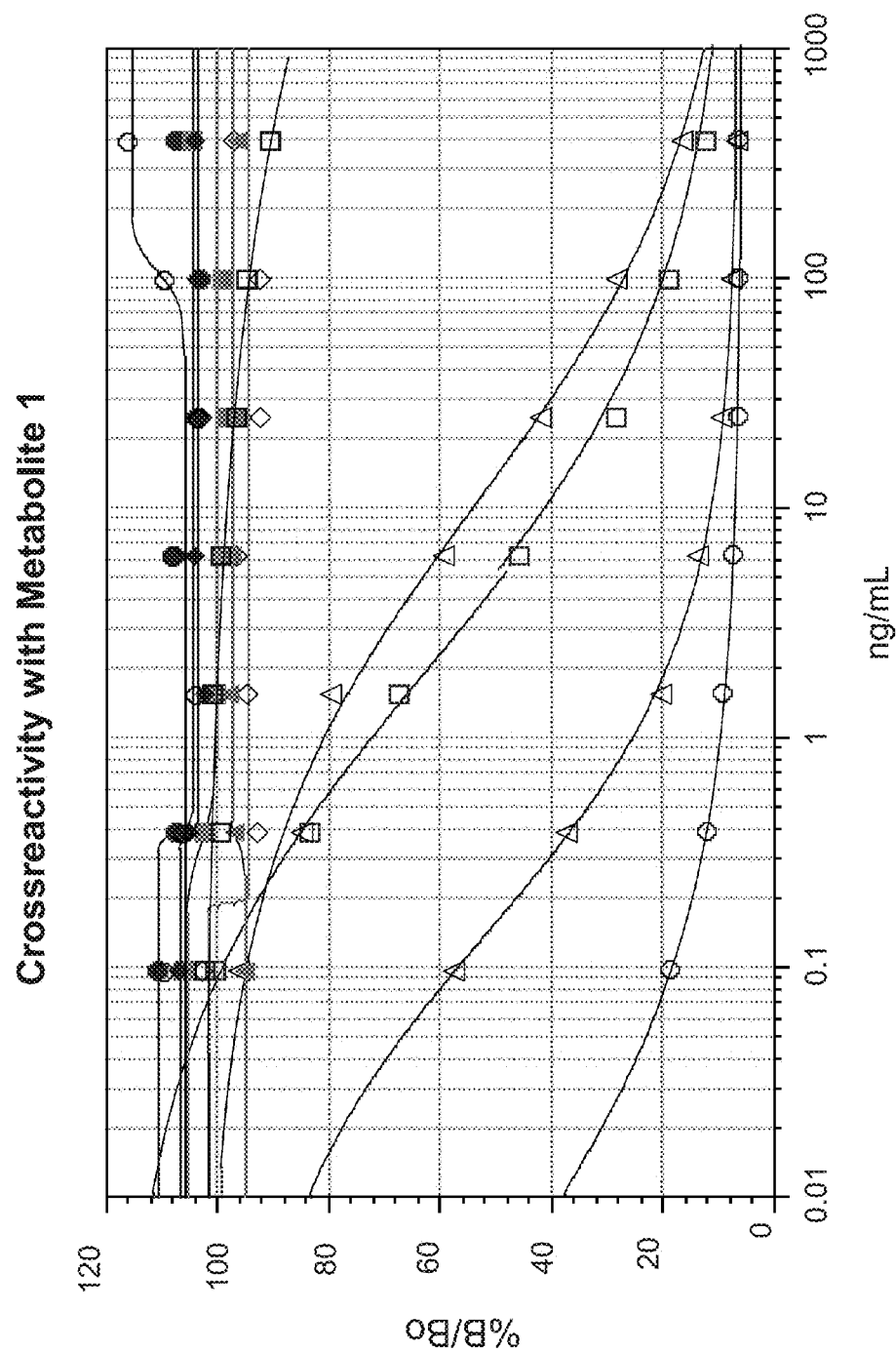
FIG. 3 is a graph depicting cross reactivity of selected anti-tofacitinib antibodies to metabolite 1 as determined by ELISA.

FIG. 3 is a graph depicting cross reactivity of selected anti-tofacitinib antibodies to metabolite 1 as determined using the competitive immunoassay. As demonstrated in FIG. 3, four antibodies demonstrated cross reactivity to metabolite 1 in a concentration dependent manner (e.g., clones 7C10.C11, 1B2.B9, 11G10.F12, and 8B5.F2). Seven clones were selective in that they bound tofacitinib but did not detectably bind metabolite 1, e.g., 5A3.E5, 10A6.C5, 10F10.H5, 6D9.A5 (or 6D9.A8), 12H4.G2, 16F10.E6, and 12D4.G6. These plots for the seven clones are shown as the lines going approximately straight across the top of the graph depicted in FIG. 3. More specifically, the data used to prepare the graph shown in FIG. 3 are as follows:

TABLE 1

| Symbol | 4-P Fit: y = (A − D)/(1 + (X/C)^B) + D: | A | B | C | D | $R^2$ |
|---|---|---|---|---|---|---|
| ○ | Plot#1 (Clone 7C10.C11: Concentration vs % B/B$_0$) | 82.2 | 0.574 | 0.00544 | 4.46 | 1 |
| □ | Plot#2 (Clone 1B2.B9: Concentration vs % B/B$_0$) | 118 | 0.526 | 2.06 | 5.47 | 0.999 |
| Δ | Plot#3 (Clone 11G10.F12: Concentration vs % B/B$_0$) | 102 | 0.544 | 10.6 | 5.08 | 0.996 |
| ◇ | Plot#4 (Clone 5A3.E5: Concentration vs % B/B$_0$) | 102 | 63.9 | 0.191 | 94.2 | 0.703 |
| ● | Plot#5 (Clone 10A6.C5: Concentration vs % B/B$_0$) | 111 | 20.5 | 0.389 | 104 | 0.46 |
| ■ | Plot#6 (Clone 10F10.H5: Concentration vs % B/B$_0$) | 106 | 4.18 | 0.345 | 100 | 0.539 |
| ▲ | Plot#7 (Clone 6D9.A8: Concentration vs % B/B$_0$) | 95 | 13.4 | 0.354 | 97.6 | 0.635 |
| ♦ | Plot#8 (Clone 12H4.G2: Concentration vs % B/B$_0$) | 107 | 21.2 | 0.383 | 103 | 0.803 |
| ○ | Plot#9 (Clone 16F10.E2: Concentration vs % B/B$_0$) | 106 | 6.41 | 107 | 116 | 0.74 |
| □ | Plot#10 (Clone 12D4.G6: Concentration vs % B/B$_0$) | 103 | 0.288 | $2.14 \times 10^7$ | −192 | 0.954 |
| △ | Plot#11 (Clone 8B5.F2: Concentration vs % B/B$_0$) | 96.4 | 0.677 | 0.144 | 6.44 | 0.999 |

The seven clones that did not show cross reactivity with Metabolite 1 were further tested for inhibition with the parent drug.

The amino acid sequences of the heavy and light chain variable domains of the seven monoclonal antibody clones that did not show cross reactivity with Metabolite-1 are provided in Table 2 below.

TABLE 2

| Antibody | Heavy Chain V domain (CDR$^a$ (bold)) | Light Chain V domain (CDR (bold)) |
|---|---|---|
| 5A3.E5 | EVKLVESGGGLVQPGGSLRLSCATSGFTFNDYYMTWVRQPPGKALEWLGFIRNKADGYTPYYSPSVKGRFTISRDNSQSILYLQMNTLRTEDSATYYCARPHYYGFPFGYWGQGTLVTVSA (SEQ ID NO: 1) | QAVVTQESALTTSPGETVTLTCRSSTGAVTTNNYANWVQEKPDHLFTGLIGGTNSRAPGVPARFSGSLIGDKAALTITGAQTEDEAMYFCALWYSNHWVFGGGTKLTVL (SEQ ID NO: 2) |
| CDR1 | GFTFNDYY (SEQ ID NO: 13) | TGAVTTNNY (SEQ ID NO: 16) |
| CDR2 | IRNKADGYTPGTN (SEQ ID NO: 14) | (SEQ ID NO: 17) |
| CDR3 | ARPHYYGFPFGY (SEQ ID NO: 15) | ALWYSNHWV (SEQ ID NO: 18) |
| 10A6.C5 | DVQLQESGPDLVKPSQSLSLTCTVTGYSITSGYSWNWIRQFPGNTLEWMGYIHYSGSTNYNPSLKSRISITRDTSKNQFFLQLNSVTTEDTATYYCVRGPYGSSFYWGQGTTLTVSS (SEQ ID NO: 3) | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIKR (SEQ ID NO: 4) |
| CDR1 | GYSITSGYS (SEQ ID NO: 19) | ENVVTY (SEQ ID NO: 22) |
| CDR2 | IHYSGST (SEQ ID NO: 20) | GAS (SEQ ID NO: 23) |
| CDR3 | VRGPYGSSFY (SEQ ID NO: 21) | GQGYSYPYT (SEQ ID NO: 24) |
| 10F10.H5 | DVQLQESGPDLVKPSQSLSLTCTVTGYSITSGYSWNWIRQFPGNTLEWMGYIHYSGTTNYNPSLKSRISITRDTSKNQFFLQLNSVTAEDTATYYCARGPYGSSFYWGQGTTLAVSS (SEQ ID NO: 5) | QIVLTQSPAIMSASPGEKVTVTCSASSSVSSMHWFQQKPGTSPKLWIYSTSNLASGVPTRFSGSGSGTSYSLTISRMEAEDVATYYCQQRNNYPYTFGGGTKLEIKR (SEQ ID NO: 6) |

TABLE 2-continued

| Antibody | Heavy Chain V domain (CDR[a] (bold)) | Light Chain V domain (CDR (bold)) |
|---|---|---|
| CDR1 | GYSITSGYS (SEQ ID NO: 19) | SSVSS (SEQ ID NO: 27) |
| CDR2 | IHYSGTT (SEQ ID NO: 25) | STS (SEQ ID NO: 28) |
| CDR3 | ARGPYGSSFY (SEQ ID NO: 26) | QQRNNYPYT (SEQ ID NO: 29) |
| 6D9.A5[b] | QVQLKESGPGLVAPSESLTITCTVSGFSLSRYSIHWVRQPPGKGLEWLGMIWGGGSTDYNSVLKSRLTIRKDYSKSQVFLKMNSLQTDDTAMYYCARIYYGIYWGQGTLVTVSA (SEQ ID NO: 7) | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIKR (SEQ ID NO: 4) |
| CDR1 | GFSLSRYS (SEQ ID NO: 30) | ENVVTY (SEQ ID NO: 22) |
| CDR2 | IWGGGST (SEQ ID NO: 31) | GAS (SEQ ID NO: 23) |
| CDR3 | ARIYYGIY (SEQ ID NO: 32) | GQGYSYPYT (SEQ ID NO: 24) |
| 12H4.G2 | DVQLQESGPDLVKPSQSLSLTCTVTGYSITSGYSWNWIRQFPGNTLEWMGYIHYSGSTNYNPSLKSRISITRDTSKNQFFLQLNSVTTEDTATYYCVRGPYGSSFYWGQGTTLTVSS (SEQ ID NO: 8) | QAVVTQESALTTSPGETVTLTCRSSTGAVTTSNYATWVQEKPDHLFTGLIGGTNNRAPGVPARFSGSLIGDKAALTLTGAQTEDEAIYFCALWYSNHWVFGGGTKLTVL (SEQ ID NO: 9) |
| CDR1 | GYSITSGYS (SEQ ID NO: 19) | TGAVTTSNY (SEQ ID NO: 33) |
| CDR2 | IHYSGST (SEQ ID NO: 20) | GTN (SEQ ID NO: 17) |
| CDR3 | VRGPYGSSFY (SEQ ID NO: 21) | ALWYSNHWV (SEQ ID NO: 18) |
| 16F10.E6 | DMQLQESGPDLVKPSQSLSLTCTVTGYSITSGYSWNWIRQFPGNTLEWMGYIHYSGNTVYNPSLKSRLSITRDTSKNQFFLQLNSVTTEDTATYYCVRGPYGSSFYWGQGTTLTVSS (SEQ ID NO: 10) | DIVMTQSQKFMSTSVGDRVSVTCKASQNVGTNVAWYQQKPGQSPKALIYSASYRYSGVPDRFTGSGSGTDFTLTISNVQSEDLAEYFCQQYYNYPLTFGAGTKLELKR (SEQ ID NO: 11) |
| CDR1 | GYSITSGYS (SEQ ID NO: 19) | QNVGTN (SEQ ID NO: 34) |
| CDR2 | IHYSGNT (SEQ ID NO: 20) | SAS (SEQ ID NO: 35) |
| CDR3 | VRGPYGSSFY (SEQ ID NO: 21) | QQYYNYPLT (SEQ ID NO: 36) |
| 12D4.G6 | QVQLKESGPGLVAPSQSLSITCTVSGFSLSIYSVHWVRQPPGKGLEWLGMIWGGGNTDYNSVLKSRLSISKDNSKSQVFLKVNSLQTDDTAMYYCARIYYGIFWGQGTLVTVSA (SEQ ID NO: 12) | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIKR (SEQ ID NO: 4) |
| CDR1 | GFSLSIYS (SEQ ID NO: 37) | ENVVTY (SEQ ID NO: 22) |
| CDR2 | IWGGGNT (SEQ ID NO: 38) | GAS (SEQ ID NO: 23) |
| CDR3 | ARIYYGIF (SEQ ID NO: 39) | GQGYSYPYT (SEQ ID NO: 24) |

[a]The Complementarity Determining Regions (CDRs) are highlighted in BOLD and underline as determined by the IMGT numbering system (Lefranc, M.-P. et al., 1999, Nucleic Acids Research 27: 209-212).
[b]Antibody clones 6D9.A8 and 16F10.E2 failed to survive the archival process. For this reason, clones 6D9.A5 and 16F10.E6, subcloned from the same parental lines, were sequenced.

Example 8

Antigen Competition

For this example, a competitive immunoassay format was used to determine whether tofacitinib inhibited the ability of the selected antibody clones that did not cross react with Metabolite-1 to bind biotinylated tofacitinib. The selected antibody clones that did not cross react with Metabolite-1 were assayed at their EC50 dilution, determined from the initial antibody titration (see FIG. 2). 200 μl/well of mixture containing anti-tofacitinib MAb (1/100 to 1/1638400 dilution), biotinylated tofacitinib (1 ng/ml), and unlabeled tofacitinib (1000 to 0.001 ng/ml) was added into goat anti-mouse IgG pre-coated plates, and incubated for 1-2 hour at room temperature. After washing the plates, 200 μl of streptavidin-HRP (50 ng/ml) was added and then incubated for 0.5-1 hour at room temperature. After washing the plates again, 200 μl of TMB substrate was added, then developed for 30 minutes, and stopped by adding 50 μl 2N sulfuric acid. Absorbance at 450 nm was measured.

As demonstrated in Table 3 below, competition was seen with clones 6D9.A8 and 12D4.G6. Specifically, inhibition of binding to biotinylated tofacitinib by unlabeled tofacitinib was observed with clones 6D9.A8 and 12D4.G6, with an ED50 of 202 ng/mL and 104 ng/mL, respectively. Table 3 below shows the ED20, ED50 and ED80 for this experiment.

TABLE 3

Antigen Competition Assay Results

| Clone | EC50 Dilution | Bo (OD450 nm) | ED20 (ng/mL) | ED50 (ng/mL) | ED80 (ng/mL) |
|---|---|---|---|---|---|
| 6D9.A8 | 3785 | 0.517 | 1092 | 202 | 34 |
| 12D4.G6 | 5449 | 1.588 | 457 | 104 | 24 |

Example 9

Binding of Anti-tofacitinib Monoclonal Antibodies to Metabolite 1 and Metabolite 2

Two clones, 6D9.A8 and 12D4.G6, were tested for cross reactivity to metabolites 1 and 2. In this experiment, the metabolites were prepared at concentrations of 200,000 to 200 ng/ml and the antibody clones were prepared at their EC50 dilutions shown in Table 1. The metabolites were incubated with biotinylated tofacitinib (1 ng/mL) and antibody on a pre-coated goat anti-mouse IgG plate for one hour. After having washed away any unbound substances, the binding of biotinylated tofacitinib to antibody was measured after the addition of streptavidin-HRP and the related chromogenic substrate TMB according to known methods.

Table 4 below summarizes the cross reactivity of clones 6D9.A8 and 12D4.G6 to Metabolite-1 and Metabolite-2.

TABLE 4

Clone cross reactivity to Metabolite 1 and Metabolite 2

| Clone | Antigen ED50 | Metabolite-1 Cross reactivity | Metabolite-2 Cross reactivity |
|---|---|---|---|
| 6D9.A8 | 234 ng/mL | 3.68% | 0.38% |
| 12D4.G6 | 152 ng/mL | 4.17% | 0.15% |

As shown in Table 4, clone 6D9.A8 showed 3.68% and 0.38% cross reactivity to Metabolites 1 and 2, respectively; and clone 12D4.G6 showed 4.17% and 0.15% cross reactivity to Metabolites 1 and 2, respectively. These data demonstrate that these antibodies do not substantially bind to metabolites 1 and 2.

Example 10

Standard Curve with Tofacitinib

Figure 4:
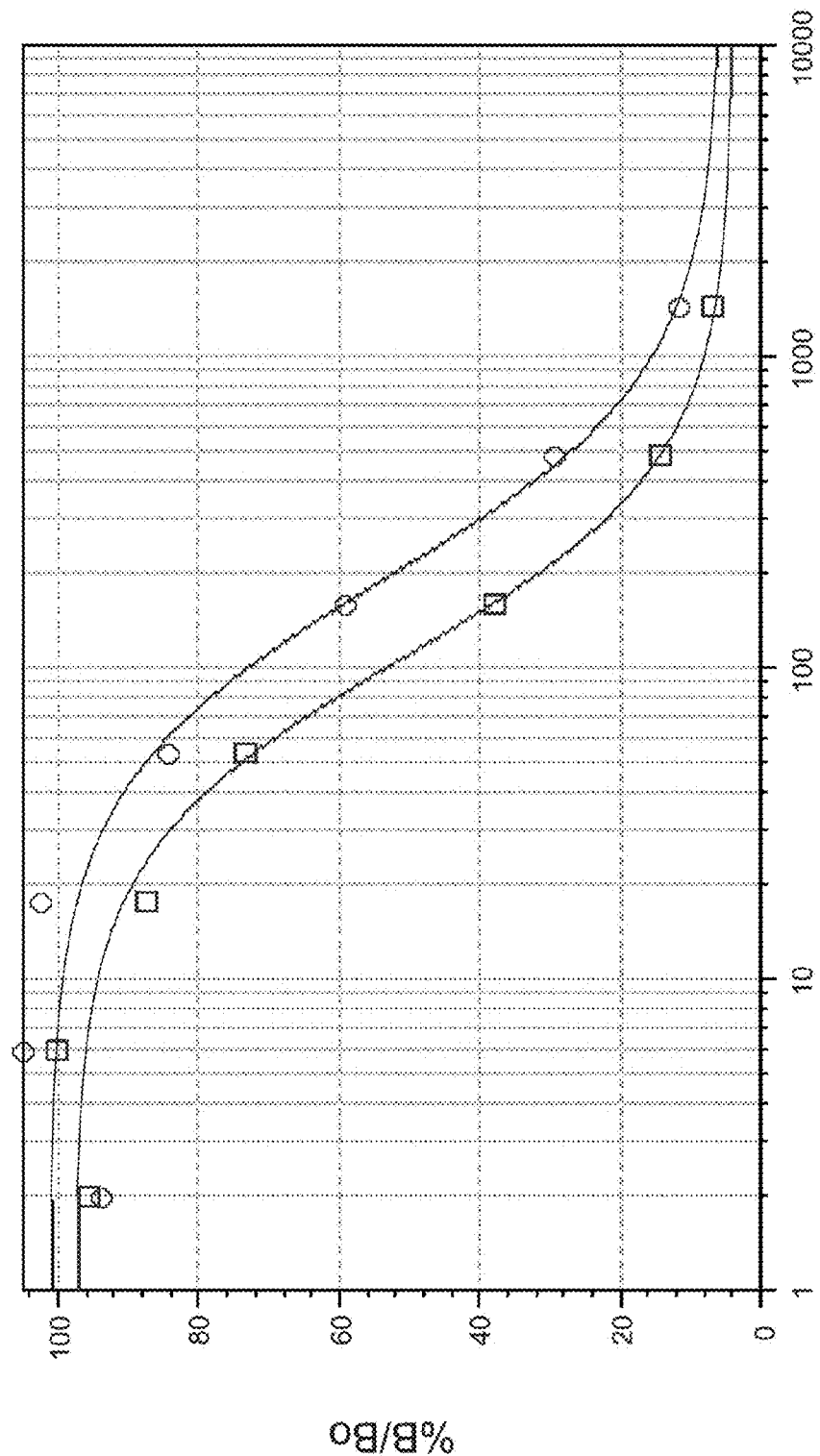
FIG. 4 is a graph depicting optimal dilution ranges of select monoclonal antibodies of the invention as determined by ELISA.

For this example, the relative affinity of a selected antibody to tofacitinib was determined using solutions containing known concentration of labeled tofacitinib (e.g., 0.001 to 1000 ng/ml). FIG. 4 is a graph depicting optimal dilution ranges of select monoclonal antibodies of the invention, e.g., 6D9.A8 (open circles) and 12D4.G6 (open squares) as determined by ELISA. Table 5 summarizes the assay conditions and results of the ELISA. Table 6 shows the data values used to generate the graph shown in FIG. 5.

TABLE 5

| Clone | Antibody Dilution | Biotinylated Tofacitinib | Standard Range |
|---|---|---|---|
| 6D9.A8 | 4,000 | 1 ng/mL | 15-1215 ng/mL |
| 12D4.G6 | 22,000 | 1 ng/mL | 5-405 ng/mL |

TABLE 6

| Symbol | 4-P Fit: y = (A − D)/ (1 + (X/C)^B) + D: | A | B | C | D | $\hat{R}2$ |
|---|---|---|---|---|---|---|
| ○ | Clone 6D9.A8 (6D9.A8_1 ng/ml_1:3785:Concentration | 101 | 1.32 | 195 | 5.55 | 0.987 |
| □ | Clone 12D4.G6 (12D4.G6_1 ng/ml_1:21796:Concentration | 97.5 | 1.39 | 109 | 3.85 | 0.997 |

Curve Fit Option—Fixed Weight Value. Subclones 6D9.A8 and 12D4.G6 demonstrated similar dose responses to the parent drug with 6D9.A8 being slightly more potent.

As demonstrated in FIG. 4 and Table 5, clone 12D4.G6 showed standard range of 5 to 405 ng/ml (FIG. 4), demonstrating that this monoclonal antibody is capable of detecting tofacitinib at levels as low as 5 ng/ml. FIG. 4 also showed standard range of 6D9.A8 was 15-1215 ng/ml. Thus, combined use of these two antibodies provides a dose range for detection of tofacitinib in a sample of from about 5 ng/ml to about 1215 ng/ml.

Example 11

Spike and Recovery in Heparinized Human Plasma

For this example, tofacitinib was spiked into commercially available heparin human plasma to determine the effect of dilution on linearity and recovery of tofacitinib in human plasma sample. Tofacitinib was spiked into Heparin-plasma (human) at a concentration of 4864 ng/ml and serially diluted 2-fold to test assay tolerance to plasma. Percent dilution linearity and percent recovery was calculated via an ELISA assay as described in Example 5.

TABLE 7

The effect of dilution on linearity and recovery of tofacitinib in human plasma sample.

| Dilution Factor | Observed Value Ng/ml | Nominal Value Ng/ml | % Dilution Linearity | % Recovery |
|---|---|---|---|---|
| 2 | >LOD[a] | 2432 | — | — |
| 4 | >LOD | 1216 | — | — |
| 8 | 745 | 604 | 106 | 123 |
| 16 | 390 | 304 | 111 | 128 |
| 32 | 183 | 152 | 104 | 120 |
| 64 | 84 | 76 | 95 | 111 |
| 128 | 46 | 38 | 105 | 121 |
| 256 | 22 | 19 | 100 | 116 |
| | | mean | 103 | 120 |

[a]LOD = level of detection

As Table 7 demonstrates, plasma samples obtained from a commercial source that were diluted at least 1:8 in assay buffer had acceptable dilution linearity and recovery. Samples diluted 2- and 4-fold returned lower than expected absorbance values, indicating sample matrix interference at these lower dilutions. These data demonstrate that the antibodies of the invention can accurately detect presence and concentration of tofacitinib even in a complex biological sample such as, but not limited to, plasma.

Example 12

Clone 6D9.A5 Characterization

For this example, tofacitinib dose response curves (0.001 to 1000 ng/ml) were run in the assay using antibody clones 6D9.A5, 6D9.A8, or 12D4.G6. The results, are shown in the Table 8 and FIG. 5. Further, the data used to generate the graph shown in FIG. 5 are set forth below in Table 9. The data disclosed herein indicate that 6D9.A5 has same standard range (15-1215 ng/ml) as 6D9.A8 and is capable of detecting tofacitinib in a sample at concentrations as low as about 15 ng/ml and as high as about 1215 ng/ml.

TABLE 8

| Clone # | Antibody Dilution | 0 ng/m standard with 2 ng/ml tofacitinib (OD 450 nm) | Tofacitinib ED50 (ng/ml) |
|---|---|---|---|
| 6D9.A5 | 1:25,600 | 1.393 | 244 |
| 6D9.A8 | 1:4,000 | 2.098 | 230 |
| 12D4.G6 | 1:22,000 | 0.623 | 118 |

TABLE 9

| Symbol | 4-P Fit: $y = (A - D)/(1 + (X/C)^B) + D$: | A | B | C | D | $R^2$ |
|---|---|---|---|---|---|---|
| ○ | Plot#1 (Standard_6D9.A5: Concentration vs % $B/B_0$) | 98.1 | 1.14 | 224 | 6.43 | 0.999 |
| □ | Plot#2 (Standard_6D9.A8: Concentration vs % $B/B_0$) | 94.6 | 1.17 | 215 | 8.83 | 1 |

TABLE 9-continued

| Symbol | 4-P Fit: $y = (A - D)/(1 + (X/C)^B) + D$: | A | B | C | D | $R^2$ |
|---|---|---|---|---|---|---|
| △ | Plot#3 (Standard_12D4.G6: Concentration vs % $B/B_0$) | 94.9 | 1.07 | 108 | 9.12 | 1 |

Curve Fit Option—Fixed Weight Value.

Thus, the replacement subclone antibody 6D9.A5 (replacing 6D9.A8) demonstrated a similar dose response activity to the parent drug as compared to subclone antibody 6D9.A8. In addition, the data disclosed herein demonstrate that 6D9.A5 and 6D9.A8 antibodies are similarly more potent binders of the parent drug compared with antibody 12D4.G6.

6D9.A5 antibody was further characterized by measuring cross reactivity to the metabolites using competitive immunoassay-3, wherein tofacitinib metabolites were used as competitors or using direct ELISA assay mentioned in Example 5, wherein the microtiter plates were coated with tofacitinib-BSA conjugate. The data shown in Table 10 demonstrate that clone 6D9.A5 had similar cross reactivity to the metabolites as observed with clone 6D9.A8 and clone 12D4.G6. That is, like 12D4.G6, 6D9.A5 did not substantially bind metabolite 1 or 2.

TABLE 10

| Clone | Antigen ED50 | Metabolite 1 Cross reactivity | Metabolite 2 Cross reactivity |
|---|---|---|---|
| 6D9.A5 | 244 ng/ml | 4.47% | <0.01% |
| 6D9.A8 | 230 ng/mL | 3.68% | 0.38% |
| 12D4.G6 | 118 ng/mL | 4.17% | 0.15% |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An immunogenic tofacitinib conjugate comprising tofacitinib coupled to an immunogenic carrier, wherein the immunogenic carrier is a protein selected from the group consisting of keyhole limpet hemocyanin and bovine serum albumin, and further wherein (a) the immunogenic tofacitinib conjugate has the structure

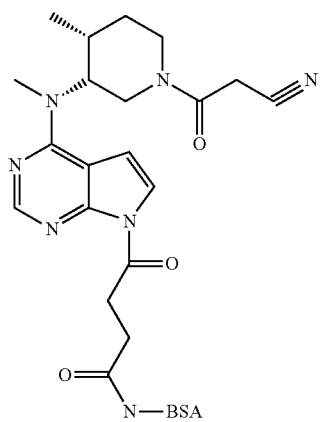

Formula V wherein BSA is bovine serum albumin; or (b) the immunogenic tofacitinib conjugate has the structure

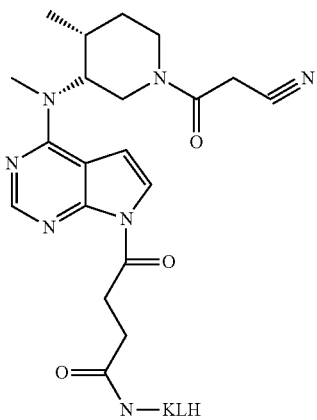

Formula VI wherein KLH is keyhole limpet hemocyanin.

2. An isolated antibody specifically binds to tofacitinib, and having greater binding affinity for tofacitinib than for tofacitinib metabolite 1 (Formula II) and tofacitinib metabolite 2 (Formula III)

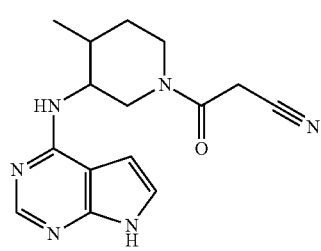

Formula II

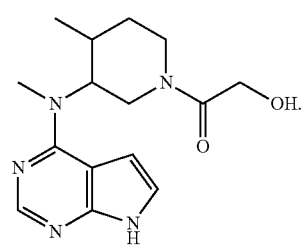

Formula III wherein the binding affinity of the antibody for the tofacitinib is 25, 30, 40, or 50 times than the binding affinity of the antibody for the metabolite 1 or metabolite 2.

3. The isolated antibody of claim 2, where the antibody is obtained using an immunogenic tofacitinib conjugate compound comprising tofacitinib coupled to an immunogenic carrier.

4. The antibody of claim 2, wherein the antibody can detect tofacitinib in a sample but not substantially detect a tofacitinib metabolite in the sample, and wherein the amount of tofacitinib ranges from about 5 ng/mL to 1215 ng/mL, from about 5 ng/mL to 405 ng/mL, or about 15 ng/mL to 1215 ng/mL.

5. A method for assessing the concentration of tofacitinib in a sample, the method comprising:

(a) providing a sample suspected of containing tofacitinib;

(b) contacting the sample or sample extract with the antibody specific for tofacitinib of claim 2 under conditions suitable for binding of the antibody to tofacitinib to form an assay mixture; and (c) detecting binding of the antibody to tofacitinib.

6. A kit for determining the amount of tofacitinib in a sample, the kit comprising:

a labeled competitor comprising tofacitinib coupled to a detectable label; and at least one selective anti-tofacitinib antibody wherein the selective anti-tofacitinib antibody has a greater binding affinity for tofacitinib than for at least one tofacitinib metabolite selected from the group consisting of tofacitinib metabolite 1 (Formula II)

and tofacitinib metabolite 2 (Formula III)

*Formula III structure* wherein the binding affinity of the antibody for the tofacitinib is 25, 30, 40, or 50 times than the binding affinity of the antibody for the metabolite 1 or metabolite 2;

wherein the labeled competitor competes with the tofacitinib in a sample for binding to the anti-tofacitinib antibody.

7. The kit of claim 6, wherein the antibody has greater binding affinity for tofacitinib than for tofacitinib metabolite 1 (Formula II) and tofacitinib metabolite 2 (Formula III)

*Formula II structure*

*Formula III structure*

8. An isolated selective anti-tofacitinib antibody that specifically binds to tofacitinib but has less than 5% cross-reactivity to at least one tofacitinib metabolite selected from the group consisting of a tofacitinib metabolite 1 (Formula II) and a tofacitinib metabolite 2 (Formula III)

*Formula II structure*

*Formula III structure* as compared to the cross-reactivity of the antibody to the tofacitinib.

9. A method of determining the amount of tofacitinib in a sample, the method comprising:
  (a) providing known amount of a labeled competitor comprising tofacitinib coupled to a detectable label;
  (b) providing the selective anti-tofacitinib antibody of claim 8;
  (c) combining the sample, the selective anti-tofacitinib antibody and the labeled competitor, wherein the tofacitinib in the sample competes with the labeled competitor for binding to the selective anti-tofacitinib antibody; and
  (d) determining the amount of tofacitinib in the sample by measuring the amount of labeled competitor not bound to antibody by detection of the label.

10. The method of claim 9, wherein the antibody has less than 5% cross-reactivity to the tofacitinib metabolite 1 (Formula II) and tofacitinib metabolite 2 (Formula III)

*Formula II structure*

*Formula III structure*

11. A competitive immunoassay kit for determining the concentration of tofacitinib in a sample, the competitive immunoassay comprising (a) at least one of the selective anti-tofacitinib antibody of claim 8;

(b) a tofacitinib compound conjugated to a detectable label, wherein the conjugated tofacitinib compound competes with the tofacitinib in the sample to bind with the antibody; and wherein the label provides a signal indicative of the concentration of tofacitinib in the sample when the tofacitinib in the sample is present in a therapeutic drug monitoring concentration.

12. The kit of claim 11, wherein the antibody has less than 5% cross-reactivity to the tofacitinib metabolite 1 (Formula II) and tofacitinib metabolite 2 (Formula III)

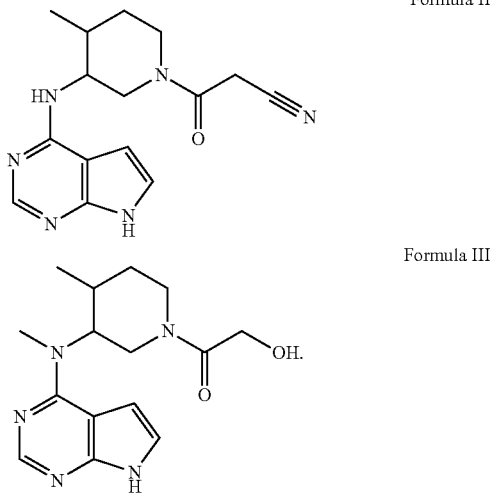

Formula II

Formula III

13. The isolated antibody of claim 8, wherein the antibody has less than 5% cross-reactivity to the tofacitinib metabolite 1 (Formula II) and the tofacitinib metabolite 2 (Formula III).

14. The antibody of claim 13, wherein the antibody is selected from the group consisting of:

(a) an antibody comprising a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24:

(b) an antibody comprising a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;

(c) an antibody comprising a heavy chain variable domain comprising an amino acid sequence selected from the group consisting of SEQ ID NO:3, SEQ ID NO:7 and SEQ ID NO:12 and further comprising a light chain variable domain comprising the amino acid sequence of SEQ ID NO:4;

(d) an antibody comprising a heavy chain variable domain comprising the amino acid sequence of SEQ ID NO:7 and further comprising a light chain variable domain comprising the amino acid sequence of SEQ ID NO:4; and (e) an antibody comprising a heavy chain variable domain comprising the amino acid sequence of SEQ ID NO:12 and further comprising a light chain variable domain comprising the amino acid sequence of SEQ ID NO:4.

15. The antibody of claim 14 (a), wherein the antibody is capable of detecting tofacitinib in a sample at a concentration ranging from about 15 ng/ml to 1215 ng/ml.

16. The antibody of claim 14 (b) wherein the antibody is capable of detecting tofacitinib in a sample at a concentration ranging from about 5 ng/ml to 405 ng/ml.

17. The kit of claim 7, wherein the kit comprises the antibody of claim 11, wherein the kit can be used to detect tofacitinib in a sample at a concentration ranging from about 5 ng/ml to about 1215 ng/ml.

18. An isolated selective anti-tofacitinib antibody having greater binding affinity for tofacitinib than for at least one tofacitinib metabolite selected from the group consisting of a tofacitinib metabolite 1 (Formula II) and tofacitinib metabolite 2 (Formula III) metabolite 1 of Formula II and a tofacitinib metabolite 2 of Formula III, the antibody comprising a heavy chain variable domain and a light chain variable domain, wherein the heavy chain variable domain comprises three complementarity determining regions (HCDR1, HCDR2, and HCDR3) selected from the group consisting of:

(a) a HCDR1 comprising an amino acid sequence selected from the group consisting of SEQ ID NO:13, SEQ ID NO:19, SEQ ID NO:30, and SEQ ID NO:37;

(b) a HCDR2 comprising an amino acid sequence selected from the group consisting of SEQ ID NO:14, SEQ ID NO:20, SEQ ID NO:25, SEQ ID NO:31, and SEQ ID NO:38;

(c) a HCDR3 comprising an amino acid sequence selected from the group consisting of SEQ ID NO:15, SEQ ID NO:21, SEQ ID NO:26, SEQ ID NO:32, and SEQ ID NO:39;

and wherein the light chain variable domain comprises three CDRs (LCDR1, LCDR2, and LCDR3) selected from the group consisting of:

(d) a LCDR1 comprising an amino acid sequence selected from the group consisting of SEQ ID NO:16, SEQ ID NO:22, SEQ ID NO:27, SEQ ID NO:33, and SEQ ID NO:34;

(e) a LCDR2 comprising an amino acid sequence selected from the group consisting of SEQ ID NO:17, SEQ ID NO:23, SEQ ID NO:28, and SEQ ID NO:35; and (f) a LCDR3 comprising an amino acid sequence selected from the group consisting of SEQ ID NO:18, SEQ ID NO:24, SEQ ID NO:29, and SEQ ID NO:34.

19. The antibody of claim 18, selected from the group consisting of (a) a HCDR1 comprising the amino acid sequence of SEQ ID NO:13, a HCDR2 comprising the amino acid sequence of SEQ ID NO:14, a HCDR3 comprising the amino acid sequence of SEQ ID NO:15, and further comprising a LCDR1 comprising the amino acid sequence of SEQ ID NO:16, a LCDR2 comprising the amino acid sequence of SEQ ID NO:17, and a LCDR3 comprising the amino acid sequence of SEQ ID NO:18;

(b) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;

(c) a HCDR1 comprising the amino acid sequence of SEQ ID NO:19, a HCDR2 comprising the amino acid sequence of SEQ ID NO:25, a HCDR3 comprising the amino acid sequence of SEQ ID NO:26, and further comprising a LCDR1 comprising the amino acid sequence of SEQ ID NO:27, a LCDR2 comprising the amino acid sequence of SEQ ID NO:28, and a LCDR3 comprising the amino acid sequence of SEQ ID NO:29;

(d) a HCDR1 comprising the amino acid sequence of SEQ ID NO:30, a HCDR2 comprising the amino acid sequence of SEQ ID NO:31, a HCDR3 comprising the amino acid sequence of SEQ ID NO:32, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;

(e) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:33, a LCDR2 comprising the amino acid sequence of SEQ ID NO:17, and a LCDR3 comprising the amino acid sequence of SEQ ID NO:18;

(f) a HCDR1 comprising the amino acid sequence of SEQ ID NO:19, a HCDR2 comprising the amino acid sequence of SEQ ID NO:20, a HCDR3 comprising the amino acid sequence of SEQ ID NO:21, and further comprising a LCDR1 comprising the amino acid sequence of SEQ ID NO:34, a LCDR2 comprising the amino acid sequence of SEQ ID NO:35, and a LCDR3 comprising the amino acid sequence of SEQ ID NO:36;

(g) a HCDR1 comprising the amino acid sequence of SEQ ID NO:37, a HCDR2 comprising the amino acid sequence of SEQ ID NO:38, a HCDR3 comprising the amino acid sequence of SEQ ID NO:39, and further comprising a LCDR1 comprising the amino acid sequence of SEQ ID NO:22, a LCDR2 comprising the amino acid sequence of SEQ ID NO:23, and a LCDR3 comprising the amino acid sequence of SEQ ID NO:24;

(h) a heavy chain variable domain comprising an amino acid sequence selected from the group consisting of SEQ ID NO:1, SEQ ID NO:3, SEQ ID NO:5, SEQ ID NO:7, SEQ ID NO:8, SEQ ID NO:10 and SEQ ID NO:12, and further comprising a light chain variable domain comprising an amino acid sequence selected from the group consisting of SEQ ID NO:2, SEQ ID NO:4, SEQ ID NO:6, SEQ ID NO:9, and SEQ ID NO:11;

(i) a heavy chain variable domain comprising the amino acid sequence of SEQ ID NO:1 and a light chain variable domain comprising the amino acid sequence of SEQ ID NO:2;

(j) a heavy chain variable domain comprising the amino acid sequence of SEQ ID NO:3 and a light chain variable domain comprising the amino acid sequence of SEQ ID NO:4;

(k) a heavy chain variable domain comprising the amino acid sequence of SEQ ID NO:7 and a light chain variable domain comprising the amino acid sequence of SEQ ID NO:4;

(l) a heavy chain variable domain comprising the amino acid sequence of SEQ ID NO:12 and a light chain variable domain comprising the amino acid sequence of SEQ ID NO:4;

(m) a heavy chain variable domain comprising the amino acid sequence of SEQ ID NO:5 and a light chain variable domain comprising the amino acid sequence of SEQ ID NO:6;

(n) a heavy chain variable domain comprising the amino acid sequence of SEQ ID NO:8 and a light chain variable domain comprising the amino acid sequence of SEQ ID NO:9;

(o) a heavy chain variable domain comprising the amino acid sequence of SEQ ID NO:10 and a light chain variable domain comprising the amino acid sequence of SEQ ID NO:11;

(p) a heavy chain variable domain comprising an amino acid sequence selected from the group consisting of SEQ ID NO3, SEQ ID NO:7 and SEQ ID NO:12 and a light chain variable domain comprising the amino acid sequence of SEQ ID NO:4; and (q) a heavy chain variable domain comprising an amino acid sequence selected from the group consisting of SEQ ID NO:3, SEQ ID NO:8, SEQ ID NO:10, and SEQ ID NO:12 and a light chain variable domain comprising an amino acid sequence selected from the group consisting of SEQ ID NO:4, SEQ ID NO:9 and SEQ ID NO:11.

20. A nucleic acid encoding an antibody of claim 19.

21. A host cell comprising the nucleic acid of claim 20.

22. A method of producing the antibody of 19, comprising culturing the host cell of claim 21 under conditions wherein the antibody is produced.

23. The method of claim 22, further comprising isolating the antibody.

* * * * *

SEQUENCE LISTING

<160> NUMBER OF SEQ ID NOS: 39

<210> SEQ ID NO 1
<211> LENGTH: 121
<212> TYPE: PRT
<213> ORGANISM: Mus musculus

<400> SEQUENCE: 1

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Asn Asp Tyr
            20                  25                  30

Tyr Met Thr Trp Val Arg Gln Pro Pro Gly Lys Ala Leu Glu Trp Leu
        35                  40                  45

Gly Phe Ile Arg Asn Lys Ala Asp Gly Tyr Thr Pro Tyr Tyr Ser Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Pro His Tyr Tyr Gly Phe Pro Phe Gly Tyr Trp Gly
            100                 105                 110

Gln Gly Thr Leu Val Thr Val Ser Ala
        115                 120

<210> SEQ ID NO 2
<211> LENGTH: 109
<212> TYPE: PRT
<213> ORGANISM: Mus musculus

<400> SEQUENCE: 2

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Asn
            20                  25                  30

Asn Tyr Ala Asn Trp Val Gln Glu Lys Pro Asp His Leu Phe Thr Gly
        35                  40                  45

Leu Ile Gly Gly Thr Asn Ser Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Met Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 3
<211> LENGTH: 117
<212> TYPE: PRT
<213> ORGANISM: Mus musculus

<400> SEQUENCE: 3

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp Asn Trp Ile Arg Gln Phe Pro Gly Asn Thr Leu Glu Trp
        35                  40                  45

Met Gly Tyr Ile His Tyr Ser Gly Ser Thr Asn Tyr Asn Pro Ser Leu
            50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Val Arg Gly Pro Tyr Gly Ser Ser Phe Tyr Trp Gly Gln Gly Thr Thr
                100                 105                 110

Leu Thr Val Ser Ser
        115

<210> SEQ ID NO 4
<211> LENGTH: 108
<212> TYPE: PRT
<213> ORGANISM: Mus musculus

<400> SEQUENCE: 4

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Gly Tyr Ser Tyr Pro Tyr
                 85                  90                  95

Thr Phe Gly Gly Gly Thr Lys Leu Glu Ile Lys Arg
                100                 105

<210> SEQ ID NO 5
<211> LENGTH: 117
<212> TYPE: PRT
<213> ORGANISM: Mus musculus

<400> SEQUENCE: 5

Asp Val Gln Leu Gln Glu Ser Gly Pro Asp Leu Val Lys Pro Ser Gln
 1               5                  10                  15

Ser Leu Ser Leu Thr Cys Thr Val Thr Gly Tyr Ser Ile Thr Ser Gly
                20                  25                  30

Tyr Ser Trp Asn Trp Ile Arg Gln Phe Pro Gly Asn Thr Leu Glu Trp
            35                  40                  45

Met Gly Tyr Ile His Tyr Ser Gly Thr Thr Asn Tyr Asn Pro Ser Leu
        50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Ala Glu Asp Thr Ala Thr Tyr Tyr Cys
                 85                  90                  95

Ala Arg Gly Pro Tyr Gly Ser Ser Phe Tyr Trp Gly Gln Gly Thr Thr
                100                 105                 110

Leu Ala Val Ser Ser
        115

<210> SEQ ID NO 6

```
<211> LENGTH: 107
<212> TYPE: PRT
<213> ORGANISM: Mus musculus

<400> SEQUENCE: 6

Gln Ile Val Leu Thr Gln Ser Pro Ala Ile Met Ser Ala Ser Pro Gly
1               5                   10                  15

Glu Lys Val Thr Val Thr Cys Ser Ala Ser Ser Ser Val Ser Ser Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Thr Arg Phe Ser Gly Ser
        50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Arg Asn Asn Tyr Pro Tyr Thr
                85                  90                  95

Phe Gly Gly Gly Thr Lys Leu Glu Ile Lys Arg
            100                 105

<210> SEQ ID NO 7
<211> LENGTH: 114
<212> TYPE: PRT
<213> ORGANISM: Mus musculus

<400> SEQUENCE: 7

Gln Val Gln Leu Lys Glu Ser Gly Pro Gly Leu Val Ala Pro Ser Glu
1               5                   10                  15

Ser Leu Thr Ile Thr Cys Thr Val Ser Gly Phe Ser Leu Ser Arg Tyr
                20                  25                  30

Ser Ile His Trp Val Arg Gln Pro Pro Gly Lys Gly Leu Glu Trp Leu
            35                  40                  45

Gly Met Ile Trp Gly Gly Gly Ser Thr Asp Tyr Asn Ser Val Leu Lys
        50                  55                  60

Ser Arg Leu Thr Ile Arg Lys Asp Tyr Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ile Tyr Tyr Gly Ile Tyr Trp Gly Gln Gly Thr Leu Val Thr Val
            100                 105                 110

Ser Ala

<210> SEQ ID NO 8
<211> LENGTH: 117
<212> TYPE: PRT
<213> ORGANISM: Mus musculus

<400> SEQUENCE: 8

Asp Val Gln Leu Gln Gly Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Tyr Ser Trp Asn Trp Ile Arg Gln Phe Pro Gly Asn Thr Leu Glu Trp
            35                  40                  45

Met Gly Phe Ile His Tyr Ser Gly Ser Thr Asn Tyr Asn Pro Ser Leu
        50                  55                  60

Lys Ser Arg Ile Ser Ile Thr Arg Asp Thr Ser Lys Asn Gln Phe Phe
```

```
                 65                  70                  75                  80
Leu Gln Leu Asn Ser Val Thr Thr Glu Asp Thr Ala Thr Tyr Tyr Cys
                        85                  90                  95

Val Arg Gly Pro Tyr Gly Ser Ser Phe Tyr Trp Gly Gln Gly Thr Thr
                100                 105                 110

Leu Thr Val Ser Ser
            115

<210> SEQ ID NO 9
<211> LENGTH: 109
<212> TYPE: PRT
<213> ORGANISM: Mus musculus

<400> SEQUENCE: 9

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Thr Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Leu Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 10
<211> LENGTH: 117
<212> TYPE: PRT
<213> ORGANISM: Mus musculus

<400> SEQUENCE: 10

Asp Met Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp Asn Trp Ile Arg Gln Phe Pro Gly Asn Thr Leu Glu Trp
        35                  40                  45

Met Gly Tyr Ile His Tyr Ser Gly Asn Thr Val Tyr Asn Pro Ser Leu
    50                  55                  60

Lys Ser Arg Leu Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Val Arg Gly Pro Tyr Gly Ser Ser Phe Tyr Trp Gly Gln Gly Thr Thr
                100                 105                 110

Leu Thr Val Ser Ser
            115

<210> SEQ ID NO 11
<211> LENGTH: 108
<212> TYPE: PRT
<213> ORGANISM: Mus musculus

<400> SEQUENCE: 11
```

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Tyr Pro Leu
                85                  90                  95

Thr Phe Gly Ala Gly Thr Lys Leu Glu Leu Lys Arg
            100                 105
```

<210> SEQ ID NO 12
<211> LENGTH: 114
<212> TYPE: PRT
<213> ORGANISM: Mus musculus

<400> SEQUENCE: 12

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ile Tyr
            20                  25                  30

Ser Val His Trp Val Arg Gln Pro Pro Gly Lys Gly Leu Glu Trp Leu
        35                  40                  45

Gly Met Ile Trp Gly Gly Gly Asn Thr Asp Tyr Asn Ser Val Leu Lys
    50                  55                  60

Ser Arg Leu Ser Ile Ser Lys Asp Asn Ser Lys Ser Gln Val Phe Leu
65                  70                  75                  80

Lys Val Asn Ser Leu Gln Thr Asp Asp Thr Ala Met Tyr Tyr Cys Ala
                85                  90                  95

Arg Ile Tyr Tyr Gly Ile Phe Trp Gly Gln Gly Thr Leu Val Thr Val
            100                 105                 110

Ser Ala
```

<210> SEQ ID NO 13
<211> LENGTH: 8
<212> TYPE: PRT
<213> ORGANISM: Artificial Sequence
<220> FEATURE:
<223> OTHER INFORMATION: 5A3-E5-HCDR1

<400> SEQUENCE: 13

```
Gly Phe Thr Phe Asn Asp Tyr Tyr
1               5
```

<210> SEQ ID NO 14
<211> LENGTH: 10
<212> TYPE: PRT
<213> ORGANISM: Artificial Sequence
<220> FEATURE:
<223> OTHER INFORMATION: 5A3-E5-HCDR2

<400> SEQUENCE: 14

```
Ile Arg Asn Lys Ala Asp Gly Tyr Thr Pro
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: 5A3-E5-HCDR3

<400> SEQUENCE: 15

Ala Arg Pro His Tyr Tyr Gly Phe Pro Phe Gly Tyr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: 5A3-E5-LCDR1

<400> SEQUENCE: 16

Thr Gly Ala Val Thr Thr Asn Asn Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: 5A3-E5-LCDR2

<400> SEQUENCE: 17

Gly Thr Asn
1

<210> SEQ ID NO 18
<211> LENGTH: 9
<212> TYPE: PRT
<213> ORGANISM: Artificial Sequence
<220> FEATURE:
<223> OTHER INFORMATION: 5A3-E5-LCDR3

<400> SEQUENCE: 18

Ala Leu Trp Tyr Ser Asn His Trp Val
1               5

<210> SEQ ID NO 19
<211> LENGTH: 9
<212> TYPE: PRT
<213> ORGANISM: Artificial Sequence
<220> FEATURE:
<223> OTHER INFORMATION: 10A6-C5-HCDR1

<400> SEQUENCE: 19

Gly Tyr Ser Ile Thr Ser Gly Tyr Ser
1               5

<210> SEQ ID NO 20
<211> LENGTH: 7
<212> TYPE: PRT
<213> ORGANISM: Artificial Sequence
<220> FEATURE:
<223> OTHER INFORMATION: 10A6-C5-HCDR2

<400> SEQUENCE: 20

Ile His Tyr Ser Gly Ser Thr
1               5

```
<210> SEQ ID NO 21
<211> LENGTH: 10
<212> TYPE: PRT
<213> ORGANISM: Artificial Sequence
<220> FEATURE:
<223> OTHER INFORMATION: 10A6-C5-HCDR3

<400> SEQUENCE: 21

Val Arg Gly Pro Tyr Gly Ser Ser Phe Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: 10A6-C5-LCDR1

<400> SEQUENCE: 22

Glu Asn Val Val Thr Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: 10A6-C5-LCDR2

<400> SEQUENCE: 23

Gly Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: 10A6-C5-LCDR3

<400> SEQUENCE: 24

Gly Gln Gly Tyr Ser Tyr Pro Tyr Thr
1               5

<210> SEQ ID NO 25
<211> LENGTH: 7
<212> TYPE: PRT
<213> ORGANISM: Artificial Sequence
<220> FEATURE:
<223> OTHER INFORMATION: 10F10-H5-HCDR2

<400> SEQUENCE: 25

Ile His Tyr Ser Gly Thr Thr
1               5

<210> SEQ ID NO 26
<211> LENGTH: 10
<212> TYPE: PRT
<213> ORGANISM: Artificial Sequence
<220> FEATURE:
<223> OTHER INFORMATION: 10F10-H5-HCDR3

<400> SEQUENCE: 26

Ala Arg Gly Pro Tyr Gly Ser Ser Phe Tyr
1               5                   10

<210> SEQ ID NO 27
```

```
<211> LENGTH: 5
<212> TYPE: PRT
<213> ORGANISM: Artificial Sequence
<220> FEATURE:
<223> OTHER INFORMATION: 10F10-H5-LCDR1

<400> SEQUENCE: 27

Ser Ser Val Ser Ser
1               5

<210> SEQ ID NO 28
<211> LENGTH: 3
<212> TYPE: PRT
<213> ORGANISM: Artificial Sequence
<220> FEATURE:
<223> OTHER INFORMATION: 10F10-H5-LCDR2

<400> SEQUENCE: 28

Ser Thr Ser
1

<210> SEQ ID NO 29
<211> LENGTH: 9
<212> TYPE: PRT
<213> ORGANISM: Artificial Sequence
<220> FEATURE:
<223> OTHER INFORMATION: 10F10-H5-LCDR3

<400> SEQUENCE: 29

Gln Gln Arg Asn Asn Tyr Pro Tyr Thr
1               5

<210> SEQ ID NO 30
<211> LENGTH: 8
<212> TYPE: PRT
<213> ORGANISM: Artificial Sequence
<220> FEATURE:
<223> OTHER INFORMATION: 6D9-A5-HCDR1

<400> SEQUENCE: 30

Gly Phe Ser Leu Ser Arg Tyr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: 6D9-A5-HCDR2

<400> SEQUENCE: 31

Ile Trp Gly Gly Gly Ser Thr
1               5

<210> SEQ ID NO 32
<211> LENGTH: 8
<212> TYPE: PRT
<213> ORGANISM: Artificial Sequence
<220> FEATURE:
<223> OTHER INFORMATION: 6D9-A5-HCDR3

<400> SEQUENCE: 32

Ala Arg Ile Tyr Tyr Gly Ile Tyr
1               5

<210> SEQ ID NO 33
<211> LENGTH: 9
```

```
<212> TYPE: PRT
<213> ORGANISM: Artificial Sequence
<220> FEATURE:
<223> OTHER INFORMATION: 12H4-G2-LCDR1

<400> SEQUENCE: 33

Thr Gly Ala Val Thr Thr Ser Asn Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: 16F10-E6-LCDR1

<400> SEQUENCE: 34

Gln Asn Val Gly Thr Asn
1               5

<210> SEQ ID NO 35
<211> LENGTH: 3
<212> TYPE: PRT
<213> ORGANISM: Artificial Sequence
<220> FEATURE:
<223> OTHER INFORMATION: 16F10-E6-LCDR2

<400> SEQUENCE: 35

Ser Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: 16F10-E6-LCDR3

<400> SEQUENCE: 36

Gln Gln Tyr Tyr Asn Tyr Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: 12D4-G6-HCDR1

<400> SEQUENCE: 37

Gly Phe Ser Leu Ser Ile Tyr Ser
1               5

<210> SEQ ID NO 38
<211> LENGTH: 7
<212> TYPE: PRT
<213> ORGANISM: Artificial Sequence
<220> FEATURE:
<223> OTHER INFORMATION: 12D4-G6-HCDR2

<400> SEQUENCE: 38

Ile Trp Gly Gly Gly Asn Thr
1               5

<210> SEQ ID NO 39
<211> LENGTH: 8
<212> TYPE: PRT
```

```
<213> ORGANISM: Artificial Sequence
<220> FEATURE:
<223> OTHER INFORMATION: 12D4-G6-HCDR3

<400> SEQUENCE: 39

Ala Arg Ile Tyr Tyr Gly Ile Phe
1               5
```